United States Patent
Rezaiifar et al.

(10) Patent No.: US 9,484,005 B2
(45) Date of Patent: Nov. 1, 2016

(54) TRIMMING CONTENT FOR PROJECTION ONTO A TARGET

(71) Applicant: QUALCOMM Incorporated, San Diego, CA (US)

(72) Inventors: Ramin Rezaiifar, San Diego, CA (US); Joel Simbulan Bernarte, San Diego, CA (US); Niccolo Andrew Padovani, San Diego, CA (US); Virginia Walker Keating, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 237 days.

(21) Appl. No.: 14/136,310

(22) Filed: Dec. 20, 2013

(65) Prior Publication Data

US 2015/0179147 A1    Jun. 25, 2015

(51) Int. Cl.
| | |
|---|---|
| *G09G 5/30* | (2006.01) |
| *G09G 5/373* | (2006.01) |
| *G03B 21/14* | (2006.01) |
| *G06F 3/01* | (2006.01) |
| *G06T 3/40* | (2006.01) |
| *G06T 19/00* | (2011.01) |

(Continued)

(52) U.S. Cl.
CPC ............ *G09G 5/373* (2013.01); *A61B 5/1114* (2013.01); *G03B 21/13* (2013.01); *G03B 21/142* (2013.01); *G06F 1/1694* (2013.01); *G06F 3/017* (2013.01); *G06K 9/00389* (2013.01); *G06T 3/40* (2013.01); *G06T 19/006* (2013.01); *H04N 9/3185* (2013.01); *H04N 9/3194* (2013.01); *G03B 2206/00* (2013.01); *G06K 9/00671* (2013.01); *G06T 2210/22* (2013.01); *G06T 2210/32* (2013.01); *G09G 2340/04* (2013.01); *G09G 2354/00* (2013.01)

(58) Field of Classification Search
CPC .... G09G 5/373; G06F 1/1694; G03B 21/142
USPC ........................................................ 345/625
See application file for complete search history.

(56) References Cited

U.S. PATENT DOCUMENTS

| | | | | |
|---|---|---|---|---|
| 6,753,907 | B1 * | 6/2004 | Sukthankar | .......... H04N 5/7408 348/190 |
| 2004/0233222 | A1 * | 11/2004 | Lee | ....................... G06F 3/0481 345/621 |

(Continued)

OTHER PUBLICATIONS

International Search Report and Written Opinion—PCT/US2014/069197—ISA/EPO—May 27, 2015.

(Continued)

*Primary Examiner* — Javid A Amini
(74) *Attorney, Agent, or Firm* — Kilpatrick Townsend & Stockton LLP

(57) ABSTRACT

Systems and methods are provided for trimming content for projection within the bounds of a projection target. The systems and methods trim the content for projection based on one or more characteristics of the projection target, including a shape, outline, and distance to the projection target. Moreover, the systems and methods designate void areas where no content will be projected based on the one or more characteristics, and the void areas will be generated or otherwise projected along with the content so that the content is projected onto the projection target and the void areas are projected outside of the projection target such that the projected content does not significantly spill onto surfaces or objects outside of the projection target.

32 Claims, 16 Drawing Sheets

(51) Int. Cl.
*A61B 5/11* (2006.01)
*G06F 1/16* (2006.01)
*H04N 9/31* (2006.01)
*G06K 9/00* (2006.01)
*G03B 21/13* (2006.01)

(56) References Cited

U.S. PATENT DOCUMENTS

| | | | |
|---|---|---|---|
| 2005/0213846 A1* | 9/2005 | Matsuda | G03B 21/14 382/275 |
| 2007/0271053 A1* | 11/2007 | Palmateer | B64F 5/0045 702/83 |
| 2010/0302143 A1* | 12/2010 | Spivack | A63F 13/12 345/157 |
| 2011/0050864 A1 | 3/2011 | Bond | |
| 2011/0098056 A1* | 4/2011 | Rhoads | G01C 21/20 455/456.1 |
| 2011/0261050 A1 | 10/2011 | Smolic et al. | |
| 2012/0069177 A1 | 3/2012 | Nagano et al. | |
| 2012/0069180 A1* | 3/2012 | Kawamura | G03B 21/00 348/143 |
| 2012/0092328 A1 | 4/2012 | Flaks et al. | |
| 2012/0154557 A1 | 6/2012 | Perez et al. | |
| 2012/0206452 A1 | 8/2012 | Geisner et al. | |
| 2012/0320157 A1* | 12/2012 | Junuzovic | G03B 15/05 348/46 |
| 2014/0071164 A1* | 3/2014 | Saklatvala | G06F 3/005 345/633 |
| 2014/0079225 A1* | 3/2014 | Jarske | H04R 29/00 381/56 |

OTHER PUBLICATIONS

Partial International Search Report—PCT/US2014/069197—ISA/EPO—Mar. 31, 2015.

* cited by examiner

TRIMMING CONTENT FOR PROJECTION ONTO A TARGET

TECHNICAL FIELD

Embodiments disclosed herein are generally directed to fitting projections to a projection target. In particular, embodiments disclosed herein may trim content for projection within boundaries of a target.

BACKGROUND

Personal, mobile, or pico projectors may be used along with mobile devices to project images or content from the mobile devices onto a target object. The projected images or content may provide a user with a larger view than what is currently available on their mobile device or may allow a user to share images or content from their mobile device. Mobile projectors may also be used to enhance augmented reality (AR) applications. AR is an emerging technology that allows a user to change the way that they interact with the world. AR is a live, direct or indirect view of a physical, real-world environment wherein the elements are augmented by computer-generated sensor input such as sound, video, graphics, or GPS data. In some uses, AR is enabled by a device that has an image capture device that captures images of the environment around a user and then uses object recognition algorithms for recognizing objects in the captured images for augmentation. The user may then be provided with a view of the environment around the user on a display of the device with portions of the view augmented based on the recognized objects, for example. Mobile projectors may allow for, instead of or in addition to displaying a view of the augmented environment on a screen, recognizing an object and projecting content onto the actual object.

SUMMARY

Consistent with some embodiments, there is provided a method including steps of determining a projection target, determining one or more bounds of the projection target, determining a content area and a void area based on the determined one or more bounds, determining a scaling factor, generating content for projection within the content area based on the scaling factor, and generating the void area The method may also be embodied in a tangible, non-transient computer-readable medium.

Consistent with some embodiments, there is also provided an apparatus, including a projector configured to project a content area and a void area based on one or more projection parameters of a projection target. The apparatus also includes a camera configured to capture one or more images of a field of view including the projection target, one or more processors coupled to the projector and the camera, the one or more processors configured to determine the one or more projection parameters, and a memory coupled to the one or more processors.

Consistent with some embodiments, there is further provided a system that includes a means for determining a projection target. The system also includes means for determining one or more bounds of the projection target, means for determining a content area and a void area based on the determined one or more bounds, and means for determining a scaling factor. The system further includes means for generating content for projection within the content area based on the scaling factor, and means for generating the void area.

Figure 1:
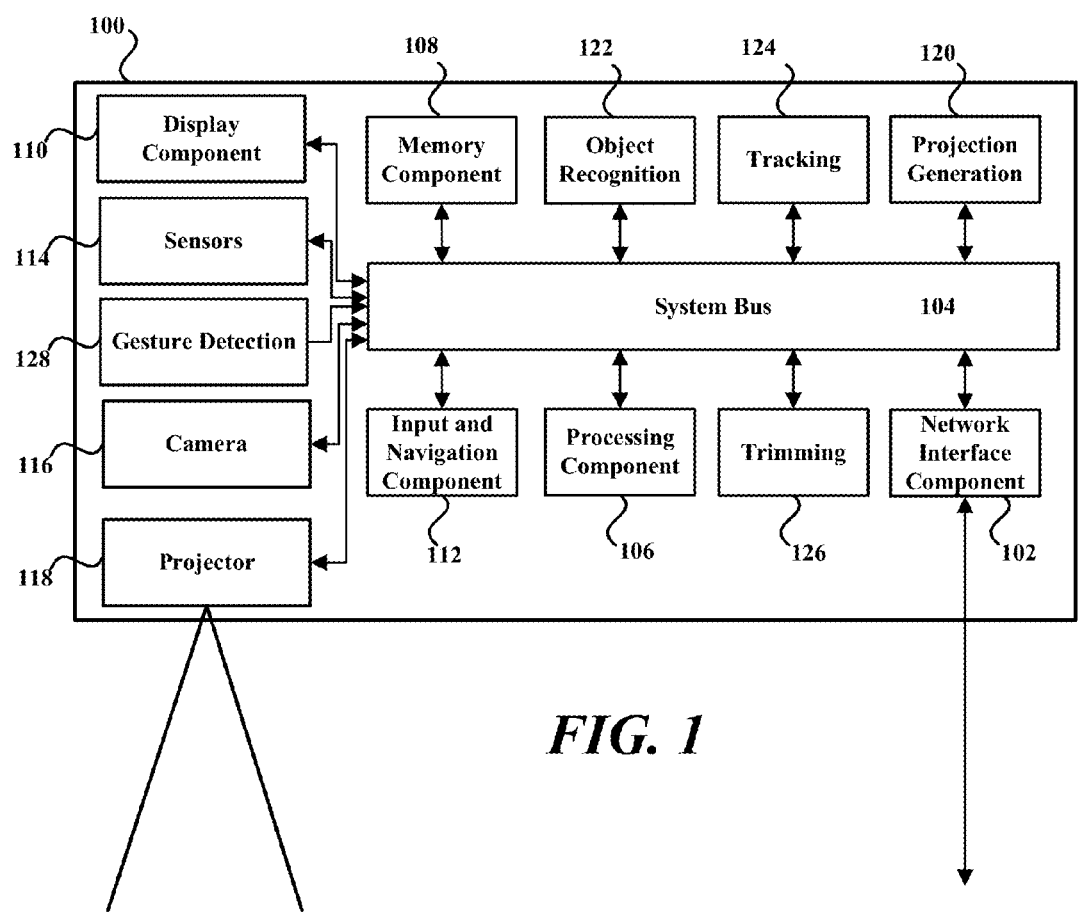
FIG. 1 is a diagram illustrating a processing system, consistent with some embodiments.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

As noted above, mobile projection devices may be used along with mobile devices to project images or content from the mobile devices onto a target object to provide a user with a larger view than what is currently available on their mobile device or to augment the target object to create an augmented reality. However, there are situations when a projection may be inconvenient for a user and even others nearby the user. For example, projections in public spaces may be distracting to others or may enable others to view private content included in the projection. Even if a user attempts to designate a projection target from which the user may only be able to view the projection, the projection may be scaled too small for the user to be able to easily view the projection or, if the projection is scaled appropriately, the projection may still overlap the target such that the projection spills onto areas beyond the target.

Accordingly, what is needed are systems and methods for trimming content within a projected image to fit within the boundaries of a specific target.

FIG. 1 is a diagram illustrating a processing system 100, consistent with some embodiments. Processing system 100 may be a mobile device such as a smartphone, a tablet computer, a personal computer, a laptop or netbooks, a set-top box (STB) such as provided by cable or satellite content providers, or a video game system consoles. Processing system 100 may also be a head-mounted display (HMD) or other wearable computing device. In some embodiments, processing system 100 is implemented in an automobile, for example in an entertainment center or console of an automobile, or is included or implemented in a healthcare device such as a smart insulin pump or smart insulin meter. According to some embodiments, processing system 100 may be implemented using any appropriate combination of hardware and/or software configured for capturing images and projecting content. In particular, processing system 100 may include any appropriate combination of hardware and/or software having one or more processors and capable of reading instructions stored on a non-transitory machine-readable medium for execution by the one or more processors for capturing images and projecting content. Some common forms of machine-readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which one or more processors or computer is adapted to read.

Processing system 100 may include network interface component 102 configured for communication with a network. Consistent with some embodiments, network interface component 102 may be configured to interface with a coaxial cable, a fiber optic cable, a digital subscriber line (DSL) modem, a public switched telephone network (PSTN) modem, an Ethernet device, and/or various other types of wired network communication devices. Network interface component 102 may also include one or more wireless transceivers, wherein each wireless transceiver may include an antenna that is separable or integral and is capable of transmitting and receiving information according to a different wireless networking protocol, such as Wi-Fi™, 3G, 4G, HSDPA, LTE, RF, NFC.

Consistent with some embodiments, processing system 100 includes a system bus 104 for interconnecting various components within processing system 100 and communicating information between the various components. In some embodiments, the bus 104 is implemented in a System on Chip (SoC) and connects various elements or components on the chip and/or cores of one or more processors. Components may include a processing component 106, which may be one or more processors, central processing units (CPUs), image signal processors (ISPs), micro-controllers, or digital signal processors (DSPs), graphics processing units (GPUs), and audio signal processors, which may include analog and/or digital audio signal processors. Components may also include a memory component 108, which may correspond to random access memory (RAM), read only memory (ROM), optical, magnetic, solid-state, or other memories such as described above.

Consistent with some embodiments, processing system 100 may also include a display component 110 for displaying information to a user. Display component 110 may be a liquid crystal display (LCD) screen, an organic light emitting diode (OLED) screen (including active matrix AMOLED screens), an LED screen, a plasma display, or a cathode ray tube (CRT) display. Display component 110 may be integrated with processing system 100, or may be separate from processing system 100 and coupled to processing system 100. Processing system 100 may also include an input and navigation component 112, allowing for a user to input information and navigate along display component 110. Input and navigation component 112 may include, for example, a keyboard or key pad, whether physical or virtual, a mouse, a trackball, or other such device, or a capacitive or other sensor-based touch screen.

Processing system 100 may also include sensors 114 that capture data associated with system 100 and/or its surroundings. Sensors 114 may include, but are not limited to, microphones or audio sensors, cameras, light sensors, proximity sensors, ambient light sensors, pressure sensors, inertial sensors (e.g., accelerometers and/or gyroscopes), magnetometers, etc. Sensors 114 may be used individually or in combinations, such as sensor arrays or any other combinations. Sensors 114 may be capable of operating interdependently or independently of one another. Sensors 114 may communicate with processing component 106 through system bus 104 in order to process data captured by sensors 114 consistent with instructions stored in, for example, memory component 108 and other modules, and to generate or otherwise obtain metadata associated with captured data.

Processing system 100 may also include a camera 116. In some embodiments, camera 116 may be a visible light camera or a depth-sensing camera, such as the Microsoft® Xbox™ Kinect™ camera. Camera 116 may also be configured to detect infrared (IR) light or ultraviolet (UV) light. Camera 116 may also be a stereo camera, a time-of-flight (ToF) camera, or other camera capable of detecting a capturing an image. In some embodiments, camera 116 may be configured to capture one or more images of objects within the field of view of camera 116 for processing. Moreover, camera 116 may be used to capture images for gesture detection, tracking, object recognition, and other purposes. Camera may also be capable of capturing a series of images, such as a video.

Processing system 100 may also include a projector 118. Projector 118 may be capable of projecting light to form one or more images. The one or more images may include content such as static or moving images that are projected as a collection of frames. In some embodiments, projector 118 may alter the placement of the projected light to give a projected image the appearance of movement or animation. Projector 118 may be a Digital Light Processing (DLP) projector, a laser beam-steering (LBS) projector, a liquid crystal on silicon (LCoS) projector, or other projector. In some embodiments, projector 118 may also be a mobile or portable projector. In some embodiments, projector 118 may be a wearable projector.

Processing system 100 may also be capable of projection generation 120, object recognition 122, tracking 124, trimming 126, and gesture detection 128. These functions may be performed by one or more software modules that perform a function when executed by processing component 106. In other embodiments, the functions may refer to a software module including an Application Specific Integrated Circuit (ASIC) or other circuit having memory and at least one processor for executing instructions to perform the function. In some embodiments, projection generation 120 may include generating one or more images for projection by projector 118. The generated one or more images may be content for projecting onto a target object or an area. In some embodiments, the content may be content for augmenting a target object or area. The content may also be images, or series of images such as a video or animation. In some embodiments, the projected content may include the projection of content generated from two-dimensional (2D) or three-dimensional (3D) data. The content may also be alerts, messages, user interface (UI) elements, social networking content, and the like. The content may also be trimmed to be projected onto a target object at a predetermined resolution which, in some embodiments, may be a maximum resolution for display on the target object.

Object recognition 122 may include performing one or more object recognition algorithms on images captured by camera 116. The object recognition algorithms performed in object recognition 122 may be capable of recognizing an object in one or more image frames using feature detection, pattern recognition, appearance matching, image matching, and the like. In some embodiments, objects recognized in object recognition 122 may be objects used for tracking 124, objects designated as targets of a projection, and objects for augmentation. In some embodiments, object recognition 122 may include automatically recognizing and designating recognized objects as targets for projection and/or augmentation.

In some embodiments, a user of processing system 100 may be capable of designating an object within a field of view as a target for projection or an object for augmentation by selecting or otherwise interacting with the object as it is displayed on processing system 100 by, for example, display component 110. If a user selects an object for augmentation, object recognition 122 may include attempting to recognize the selected object and augment the recognized object with content based on information provided by a third party or by information related to the object. In some embodiments, object recognition 122 may include communicating with a network using network interface component 102 to perform object recognition 122 and to find content related to the object.

Tracking 124 may include associating a location of objects within a target area over time. In some embodiments, tracking 124 may be configured to control a projection based on the determined location and orientation of objects in a target area over a period of time so that the projected content remains projected on one or more designated target objects even as the projector moves or the target objects move. Tracking 124 may control a projection of projector 118 based on images captured by camera 116 and, in some embodiments, information from sensors 114. In some embodiments, tracking 124 may include estimating pose, orientation, and depth information about target objects using images captured by camera 116 and/or information obtained by sensors 114, such as an accelerometer or gyroscope. Tracking 124 may further include generating one or more matrices that may later be used in projection generation 120 for controlling a projection by projector 118, including generating augmented reality content. Tracking 124 may include scaling, rotating and translating content for projection generation 120 based on captured images from camera 116 and/or information from sensors 114. Tracking 124 may include determining six degrees-of-freedom based on the captured image and tracking content for projection based on the determined six degrees-of-freedom. For embodiments where camera 116 is or includes a depth sensing camera, the one or more images may be processed to develop a depth map of the field of view. The depth map may be used in tracking 124 for tracking and controlling the projection, including maintaining a proper focus of the projection.

Trimming 126 may include performing one or more actions to trim content generated by projection generation and projected by projection device to be projected within the boundaries of a target object. In general, trimming 126 may include determining areas of a projection that will have content, which may be referred to as content areas, and void areas, which are areas of the projection that will have no content. In some embodiments, the void areas may be areas in which black or dark pixels are projected. Dark pixels may include black pixels, but may also include pixels that are darker than an average intensity of the projected content or an average intensity of edges of the projected content. In some embodiments, dark pixels may include pixels that have a color that is 80% or more dark on an RGB color scale. In some embodiments, dark pixels may include pixels that have a color that is dark relative to the color of light being projected by projector 118. In some embodiments, the void areas may be areas in which black or dark scan lines are projected. Furthermore, in some embodiments, dark pixels may be an area where no light is projected by projector 118. For example, a mirror, laser, or other component that controls a pixel may be turned off to produce a dark pixel in a void area.

In general, trimming 126 may include generating a void area to mask the projected image based on a shape or outline of the target object. For example, trimming 126 may include determining a shape of the target object, creating a void area based on the determined shape, and masking the projection so that content is projected within the determined shape and substantially no content is projected outside of the determined shape while dark pixels are projected outside the determined shape. In some embodiments, the shape may be determined by determining an outline of a target object from an image of the target object captured by camera 116. In other embodiments, the shape may be determined by determining an outline of a target object from an image of the target object that may have been stored in memory component 108 or received from another device in communication with system 100. In some embodiments, the void area may be automatically set to be slightly larger or slightly smaller than the determined outline, for example 1 pixel larger or smaller. In some embodiments, the shape may be determined by object recognition 122, wherein the target object is recognized as a known shape having a predetermined shape and outline. In some embodiments, the shape and, thus, the void area, may be set by a third party, such as a manufacturer, retailer, or content provider for the purpose of projecting specific masked content onto the target object.

Trimming 126 may also include scaling the projection based on a distance to the target object. As described previously, camera 116 may be or include a depth camera which may be capable of creating a depth map that may be used by tracking 124 for maintaining the projection at a predetermined location and at a proper focus. Trimming 126 may also use a depth map for determining a scaling factor for scaling a projection to have a desired size or resolution on a target object. Further, trimming 126 may determine a shape of the projection target using a depth map by segmenting the projection target from the background in the depth map. In some embodiments, trimming 126 scales the projection to have a resolution, such as a maximum resolution, on a target object to allow a user to view the projection at the maximum resolution. Trimming 126 may further scale the projection to have a maximum resolution within content areas, i.e., such that the projected content does not significantly spill into the void areas. Consequently, in some embodiments, trimming 126 may include determining a shape of a projection target, determining content areas and void areas for projection based on the determined shape, determining a distance to a projection target, and determining a scaling factor based on the determined distance and the determined content area. The determined content areas of content and void areas and the determined scaling factor may then be used by projection generation 120 for generating the trimmed content for projection within the bounds of the projection target at a resolution determined by the scaling factor. In some embodiments, the scaling factor may be adjusted based on user preferences or settings. For example, a user may set a particular scaling factor that will be used by projection generation 120 for generating the trimmed content for projection at a predetermined resolution determined by the set scaling factor.

In some embodiments, object recognition 122, tracking 124, and trimming 126 may be used in processing system 100 for refining content projected by projector 118. For example, camera 116 may be capable of capturing one or more images of content projected by projector 118 as well as the projection target. Object recognition 122, tracking 124, and trimming 126 may be performed on the captured one or more images to determine a scale of the projected content, a focus of the projected content, and the boundaries of the determined content areas and void areas to refine these features of the projected content. Information related to the refined features may be provided to projection generation 120 so that content having these refined features may be projected by projector 118. This refinement determination 118 may be performed at a predetermined rate related to a frame rate of the projected content or may be performed at a variable rate. For example, processing system 100 may determine a degree of refinement after each refinement determination and, as the degree becomes smaller the frequency of the refinement may be reduced. As another example, the frequency of refinement may be increased when object recognition 122 and/or tracking 124 determines a significant change in a size or location of the projection target, or a significant change in a position of system 100.

Gesture detection 128 may include detecting gestures by processing a series of images or other information captured by camera 116 and/or sensors 114 to detect an abrupt change in a statistic of data captured by camera 116 and/or sensors 114. The statistic may be a histogram, average luminance, variance of luminance, etc., and gesture detection 128 may include comparing a current statistic with a prior statistic, wherein a prior statistic may be calculated as a combination of the statistics of a set of one or more captured data acquired at times immediately preceding the current captured data from sensors 114 or image from camera 116. In some embodiments, gesture detection 128 may include comparing statistics by calculating the absolute difference, sum of absolute differences of each of a set of statistics, or sum of absolute differences of each bin of a histogram, the result of which may be compared to a threshold to exclude differences resulting from ambient lighting or device motion. Differences greater than the threshold may be classified as abrupt changes in a statistic indicative of a gesture. Gesture detection 128 may also detecting movement over time using ultrasonic waves.

In some embodiments, gesture detection 128 may include detecting gestures for initiating a projection by projector 118. Gesture detection 128 may include detecting gestures for trimming 126 the content to be projected within the bounds of a target object. In some embodiments, trimming 126 the content to be projected within the bounds of a target object may be implemented as a part of a private mode associated with system 100. Gesture detection 128 may detect one or more gestures for entering and exiting the private mode. Example gestures detected by gesture detection may include a cover gesture, which may be a hand or other control object detected in a position over system 100. Another gesture that may be detected is an open or closed hand. Another gesture may be that of a "throwing motion" with a closed hand moving away and then opening. Other gestures that may be detected may include tilting a hand or removing a hand from over system 100. Each of the gestures may be detected and gesture detection 128 may associate a specific command with each of the detected gestures. For example, a cover gesture may initiate projection, an open hand may enter a private mode or otherwise provide an indication for trimming 126 the projected content, and the throwing motion may leave the private mode or otherwise indicate that the projected content is no longer confined to the boundaries of the target object. These gestures and their associated actions are just examples. In practice, gesture detection 128 may be able to detect a gesture based on captured data and associate a command or action with the detected gesture.

Processing system 100 may include more or less components than shown in FIG. 1 according to some embodiments. Moreover, components shown in FIG. 1 may be directly coupled to one or more other components in FIG. 1, eliminating a need for system bus 104. Furthermore, components shown in FIG. 1 may be shown as being part of a unitary system 100, but may also be part of a system where the components are separate but coupled and in communication. In general, the components shown in FIG. 1 are shown as examples of components in a processing system 100 capable of performing embodiments disclosed herein. However, a processing system 100 may have more or fewer components and still be capable of performing some embodiments disclosed herein.

Figure 2A:
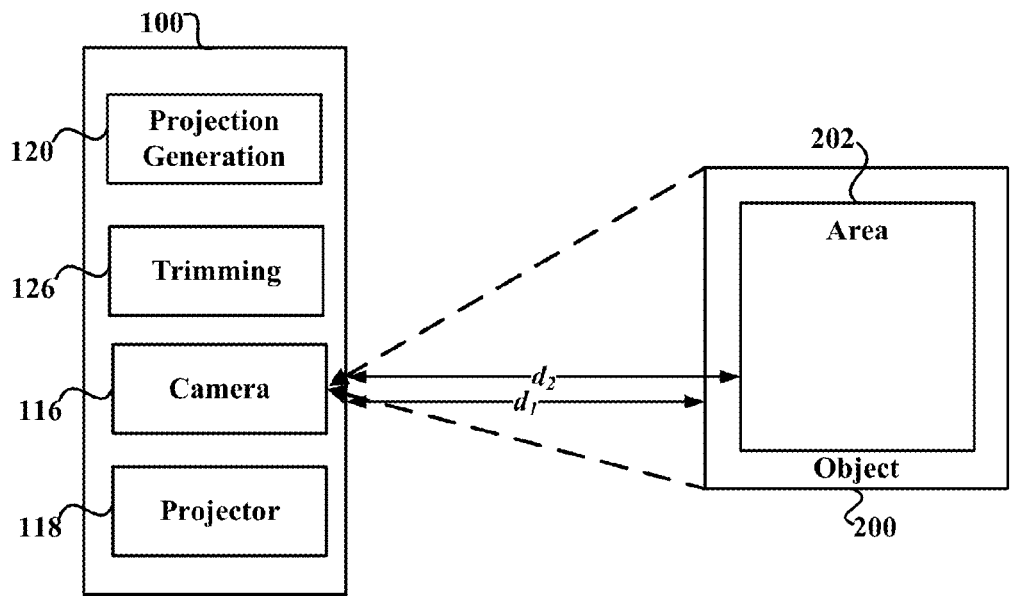
FIGS. 2A-2D illustrate an example of trimming content to fit within the bounds of an area on a target object, consistent with some embodiments.

FIGS. 2A-2D illustrate an example of trimming content to fit within the bounds of an area on a target object, consistent with some embodiments. For the purpose of illustration, only a portion of processing system 100 is shown in FIGS. 2A-2D, however reference may be made to other components of processing system 100 shown in FIG. 1. As shown in FIG. 2A, a target object 200 includes an area 202 on target object 200. Camera 116 may capture one or more images of object 200 and area 202 which may be processed for projection generation 120, object recognition 122, tracking 124, and trimming 126. In some embodiments, a capture frame may be projected onto object 200 at the time of image capture such as disclosed in copending U.S. application Ser. No. 14/038,480, filed Sep. 26, 2013, Qualcomm Ref. No. 131009, the entire contents of which are hereby incorporated by reference in their entirety.

Object recognition 122 on the one or more captured images may include attempting to recognize object 200 and/or area 202. In some embodiments, object recognition 122 may include retrieving and/or generating content for projection based on a recognized object. In some embodiments, object recognition 122 may also include designating area 202 on object 200 as a content area based on information associated with the recognized object. For example, a manufacturer, retailer, or producer of object 200 may specifically designate content for projection in area 202, which may be determined through object recognition.

Tracking 124 may include determining a pose, position, six degrees-of-freedom (DOF) and other information about object 200 and area 202. In some embodiments, camera 116 may be or include a depth camera which may be used to determine a depth map of the field of view including object 200 including a distance d1 to object 200 and a distance d2 to area 202. The depth map and the distances d1 and d2, may be used for tracking 124 of object 200 and area 202, trimming 126, and for focusing content projected on object 200 and/or area 202.

In some embodiments, a portion of object 200, such as area 202, may be designated as a content area. Area 202 may be designated as a content area by a third party, such that object recognition 122 recognizes object 200 and determines information about object 200 that includes designating area 202 as a content area, such as described previously. In some embodiments, a user of system 100 may be capable of manually designating a portion of object 200, such as area 202, as a content area. In some embodiments, the designation may be made by selecting an area displayed on display component 110 using input and navigation component 112. Trimming 126 may then include trimming content to be projected to be within the bounds of area 202.

For example, trimming 126 may include determining a shape of area 202 based on one or more images and determining the content area and the void area based on the determined shape and outline so that content may be projected within the bounds of the determined shape while no content is projected outside of the bounds of the determined shape. In some embodiments, determining the shape may include determining an outline of area 202 from one or more images of object 200 and area 202. In some embodiments, the shape and outline may be determined based on object recognition 122, wherein the target object is recognized as a known shape having a predetermined shape and outline. Trimming 126 may also include determining a scaling factor based on the distances d1 and d2 to object 200 and area 202.

Figure 2B:
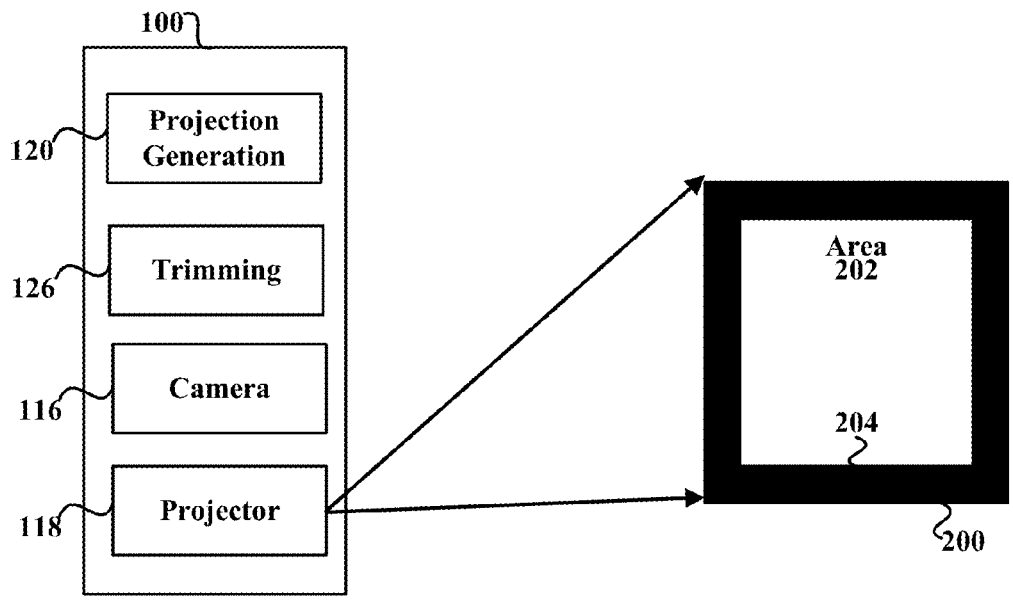

The determined content area and void area and the determined scaling factor may then be used by projection generation 120 for generating trimmed content for projection within the bounds of area 202 at a resolution determined by the scaling factor. FIG. 2B illustrates a void area 204 outside the bounds of area 202. In some embodiments, void area 204 may be a virtual mask area, where black or dark pixels are projected onto and around object 200 outside the bounds of area 202. In some embodiments, void area 204 may be black or dark scan lines that are projected during a scan projection. In other embodiments, void area 204 may be an area in which projector is configured to not project any pixels by, for example, turning off pixels in void area 204.

Figure 2C:
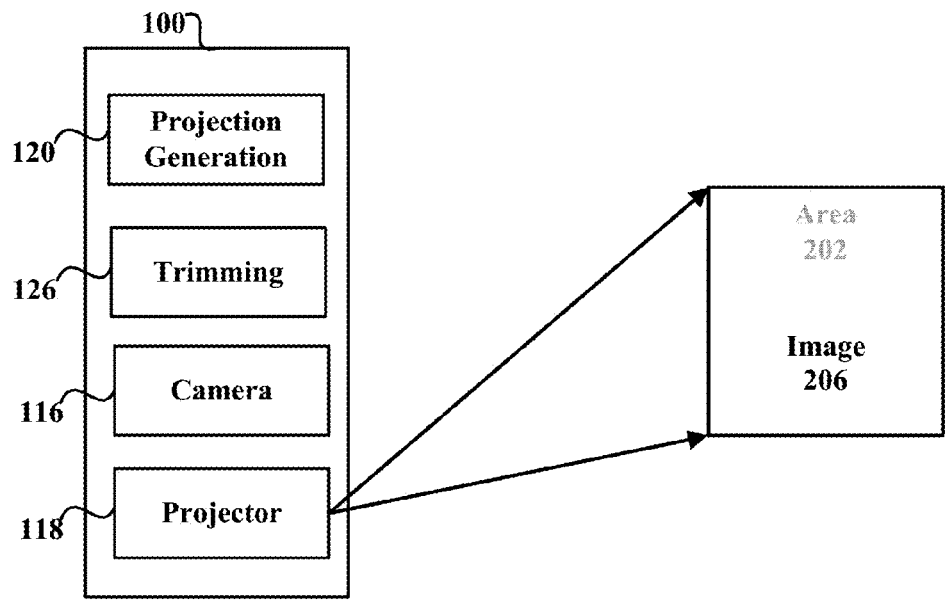
Figure 2D:
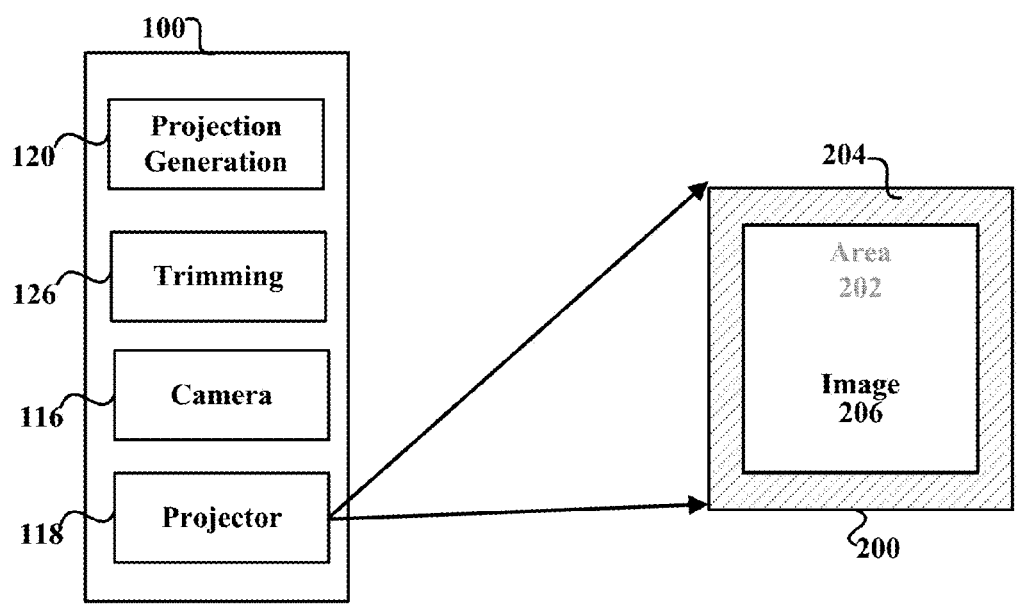

FIG. 2C illustrates projector 118 projecting an image 206. Consistent with some embodiments, image 206 may have dimensions designed to fit within bounds of area 202 at a resolution determined by the scaling factor. FIG. 2D illustrates projector 118 projecting image 206 on area 202 of object 200, with void area 204 surrounding area 202. For the purposes of illustration, it is assumed that projector 118 in FIG. 2D projects an area that has the same dimensions as object 200. However, if projector 118 projects an area that exceeds the bounds of object 200 void 204 may fill the bounds of the area outside of area 202. In some embodiments, camera 116 may continue to capture one or more images that include projected image 206 and void area 204. Tracking 124 may include adjusting the projected image 206 and the void area 204 based on images of object 200, projected image 206, and void area 204 captured by camera 116 or otherwise provided to system 100.

As shown in FIGS. 2A-2D, a user may be able to project content, such as image 206 within a predetermined area, such as area 202. For example, a user who wants to view image 206 on a larger surface area than is available on display component 110 of system 100 may be able to project image 206 onto area 202 on object 200 for viewing. The user could designate area 202 as a content area and trimming 126 may be able to determine the areas of image 206 and a void area 204 as well as a scaling factor such that image 206 is able to be projected on area 202 at a predetermined resolution which may be a maximum resolution, thus, allowing the user to view image 206 on the larger area 202. Moreover, a user would not have to be concerned about projected image 206 extending beyond the bounds of area 202, or spilling out onto surfaces behind or around object 200 as trimming 126 would determine those areas as being outside of target area 202 and, thus, generate void area 204 where no content is projected.

In some embodiments, image 206 may be an image for augmenting object 200 to create an augmented reality. For example, object recognition 122 may recognize object 200 and retrieve image 206 from a manufacturer, retailer, or producer of object 200. Trimming 126 may determine void area 204 such that the retrieved image 206 is projected on area 202 of object 200. In some embodiments, void area 204 and the area for image 206 may be retrieved along with image 206, such that the areas are predetermined by the manufacturer, retailer, or producer of object 200.

Figure 3A:
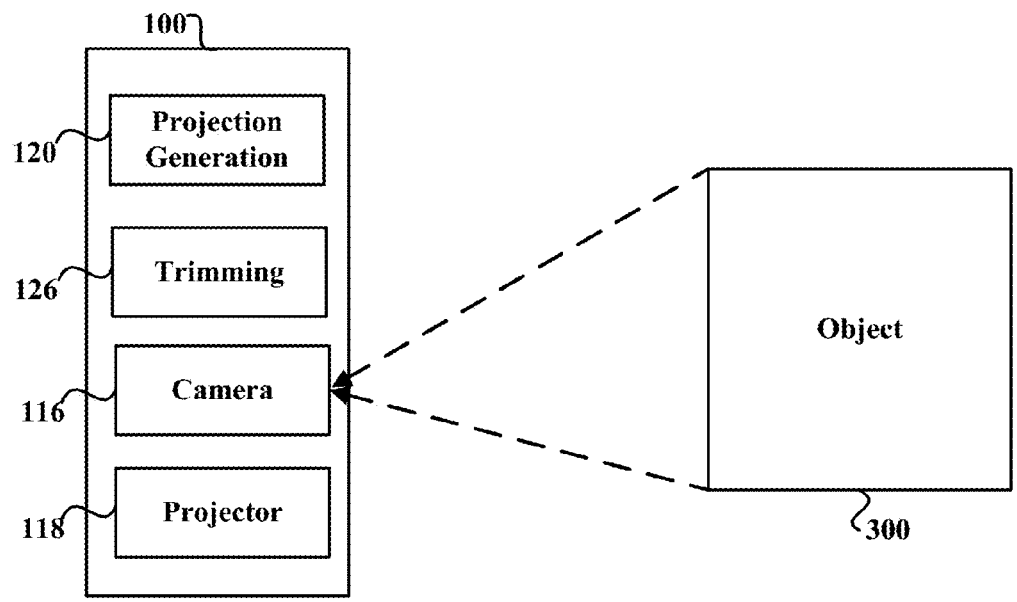
FIGS. 3A and 3B illustrate an example of trimming content to fit on an object, consistent with some embodiments.
Figure 3B:
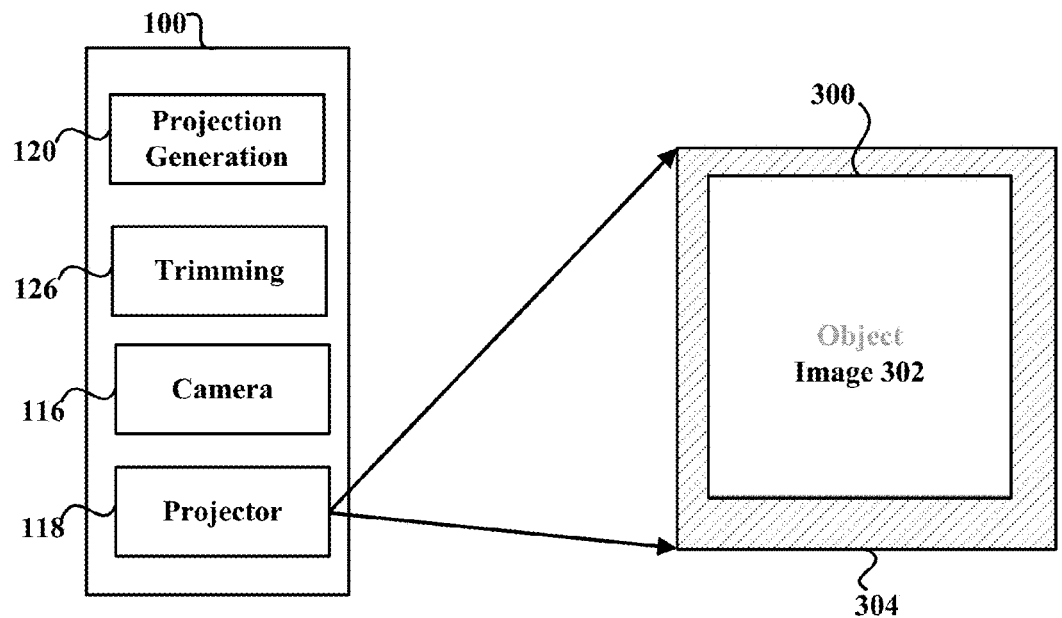

FIGS. 3A and 3B illustrate an example of trimming content to fit on an object, consistent with some embodiments. In particular, the example shown in FIGS. 3A and 3B illustrate an example of trimming content to fit within the bounds of object 300. As shown in FIG. 3A, camera 116 may capture one or more images of object 300. The one or more captured images may then be used for projection generation 120, object recognition 122, tracking 124, and trimming 126. In some embodiments, images of object 300 may be provided to system 100 or may have been stored in memory component 108 of system 100. Object recognition 122 may determine content such as image 302 for projecting onto object 300. In some embodiments, a user of system 100 may designate image 302 for projection onto object 300. Moreover, object recognition 122 may designate object 300 as a content area. For example, if image 302 is designed for display on a flat surface, object recognition 122 may attempt to determine the closest flat surface to system 100 and designate that surface as a content area. As another example, if image 302 is one of many images in a video for projection, object recognition 122 may attempt to determine a surface suitable for displaying the video. For example, object recognition 122 may attempt to locate a flat, rectangular surface, and/or a still surface, for displaying the video and designate such a surface with the field of view as a content area.

Trimming 126 may determine a shape of object 300, a shape and/or an outline of object 300, a distance to object, and determine a void area 304 and a content area for projection of image 302. As shown in FIG. 3B, projector 118 may project image 302 and void area 304 onto object 300 such that image 302 is projected within the bounds of object 300 and void area 304 is projected outside the bounds of object 300. In some embodiments, void area 304 may correspond to a virtual light mask that includes projected black or dark pixels or pixels which have been turned off by projector 118 so that no content is projected by projector 118 at those pixels. In some embodiments, image 302 may be an image for augmenting object 300 to create an augmented reality. In other embodiments, image 302 may be an image or other content that a user of system 100 wants to project on object 300, for example, to view on object 300 instead of on display component of system 100.

Figure 4A:
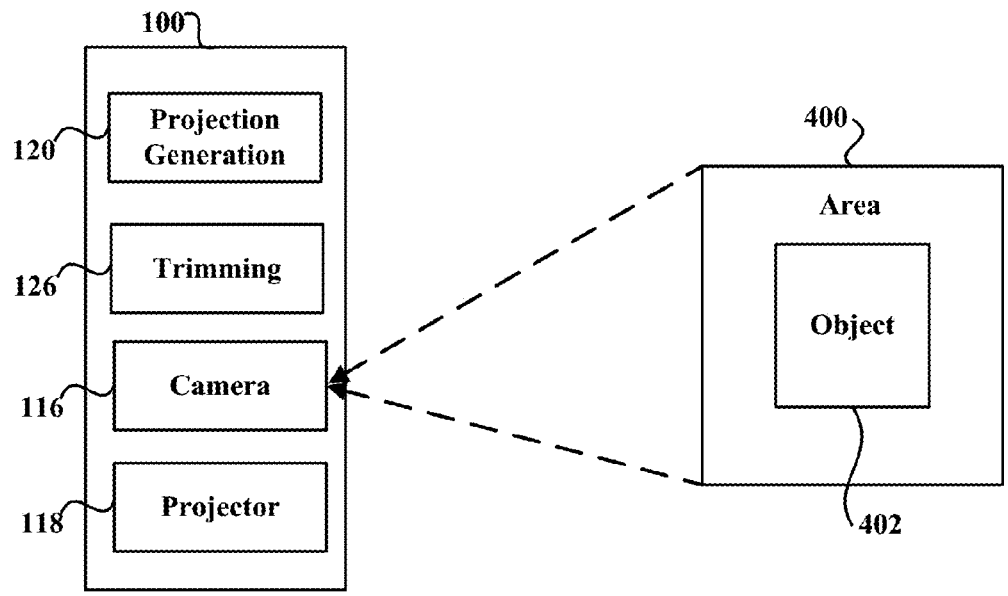
FIGS. 4A and 4B illustrate an example of trimming content to fit outside the bounds of an object, consistent with some embodiments.
Figure 4B:
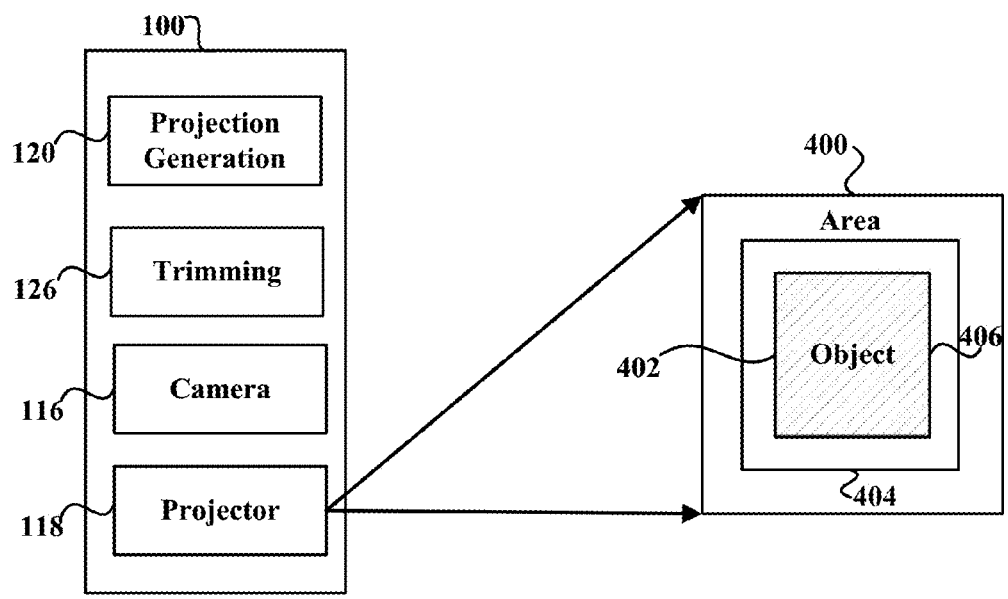

FIGS. 4A and 4B illustrate an example of trimming content to fit outside the bounds of an object 402, consistent with some embodiments. The example illustrated in FIGS. 4A and 4B may be referred to be a "reverse trimming" wherein the content is projected outside of object 402 and object 402 is masked by projecting a void area 406 on object 402. As shown in FIG. 4A, camera 116 may capture one or more images of object 402 having area 400 surrounding object 402. The one or more captured images may then be used for projection generation 120, object recognition 122, tracking 124, and trimming 126. In some embodiments, images of area 400 and object 402 may be received by system 100 or may be stored in memory component 108. Object recognition 122 may determine content such as image 404 for projecting onto area 400 around object 402. In some embodiments, a user of system 100 may designate image 404 for projection onto area 400 around object 402. Trimming 126 may determine a shape of object 402, an outline of object 402, a distance to object 402 and area 400, and determine a void area 406 and a content area for projection of image 404 onto area 400 around object 402. As shown in FIG. 4B, projector 118 may project image 404 onto area 400 and a void area 406 may be generated on object 402 such that image 404 is projected outside the bounds of object 402 and void area 406 is generated on object 402.

Generating a void area 406 to mask object 402 and projecting content such as image 404 around object 402, such as shown in FIGS. 4A and 4B may be useful for projecting information about object 402 around object 402 without obscuring object 402 or projecting content that appears to interact with object 402. For example, image 404 may include instructions for using, operating, or maintaining object 402, and may be projected around object 402 while void area 406 masks object 402 to prevent object 402 from being obscured by image 404. In another example, image 404 may interact with object 402, such as referencing object 402 or showing speech bubbles of object 402 and the like, while void area 406 masks object 402 to prevent object 402 from being obscured by image 404.

Figure 5A:
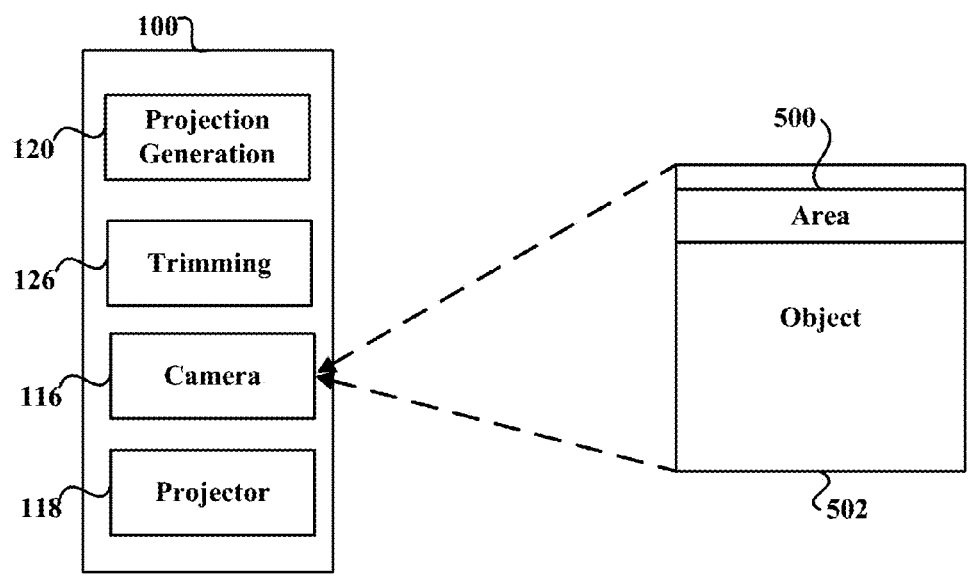
FIGS. 5A and 5B illustrate an example of trimming content, consistent with some embodiments.
Figure 5B:
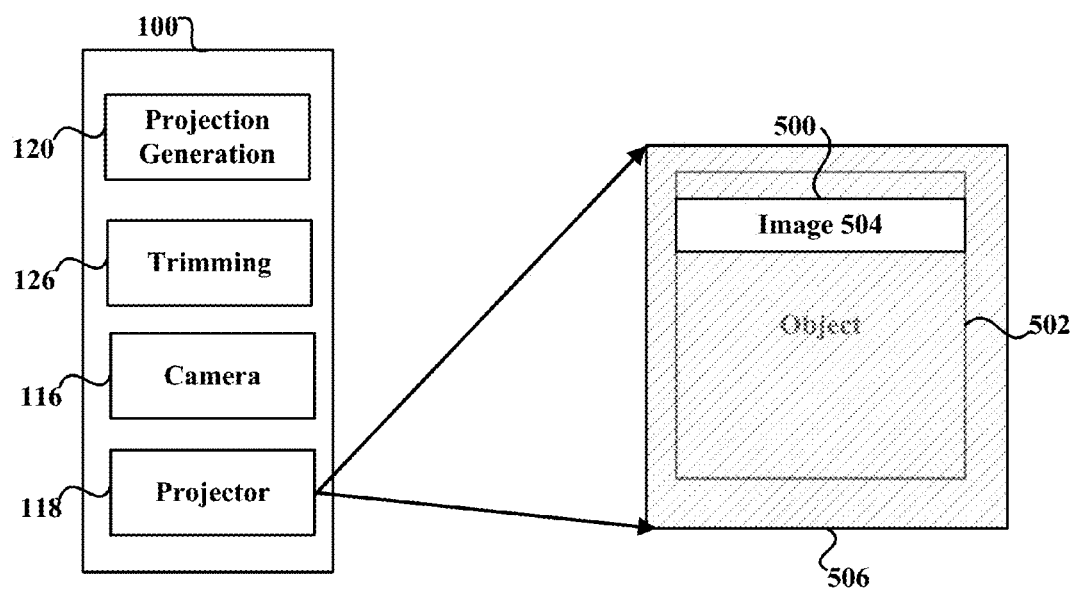

FIGS. 5A and 5B illustrate an example of trimming content, consistent with some embodiments. In particular, the example shown in FIGS. 5A and 5B illustrate an example of trimming content to fit within the bounds of area 500 on object 502. As shown in FIG. 4A, camera 116 may capture one or more images of object 502 having area 500. The one or more captured images may then be used for projection generation 120, object recognition 122, tracking 124, and trimming 126. In some embodiments, images of area 500 and object 502 may be received by system 100 or may be stored in memory component 108. In some embodiments, object recognition 122 may determine content such as image 504 for projecting onto area 500 of object 502. In some embodiments, a user of system 100 may designate image 504 for projection onto area 500 of object 502. For example, object recognition 122 may recognize object 502 as having an area 500 of blank space, and designate area 500 as a content area onto which image 504 may be projected. Alternatively, object recognition 122 may recognize object 502, and based on predetermined instructions associated with object 502, designate area 500 as a content area onto which image 504 may be projected. For example, image 504 may be content associated with object 502, such as instructions for use or information about object 502 that is tailored for projection onto area 500.

Trimming 126 may then determine a shape of area 500, an outline of area 500, a distance to object 502 and area 500, and determine a void area 506. As shown in FIG. 5B, projector 118 may project image 504 onto area 500 of object 502 and generate void area 506 such that image 504 is projected only on area 500.

In some embodiments, the examples shown in FIGS. 5A and 5B may be combined with the examples shown in FIGS. 4A and 4B such that an image could be projected on object 502 and on areas outside of object 502, such that a portion of object 502 is masked by void area 506. For example, if a user or AR content provider does not want to augment object 502 or only wants to augment a portion of object 502 but wants to augment the area around object 502, image 404 and/or 504 may be respectively projected around object 502 and on object 502. In some embodiments, system 100 may be capable of projecting multiple images and generating multiple void areas on and around an object, each of which may be tracked separately by tracking 124. In some embodiments, the multiple images and void areas may be alternatingly projected by projector 118.

Figure 6A:
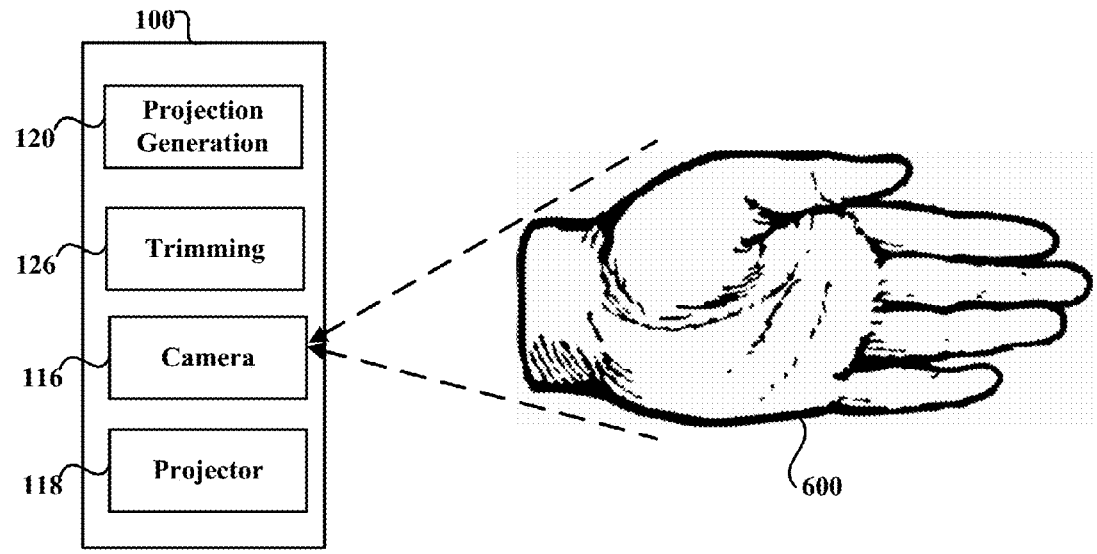
FIGS. 6A and 6B illustrate an example of trimming content to fit within the bounds of a hand.
Figure 6B:
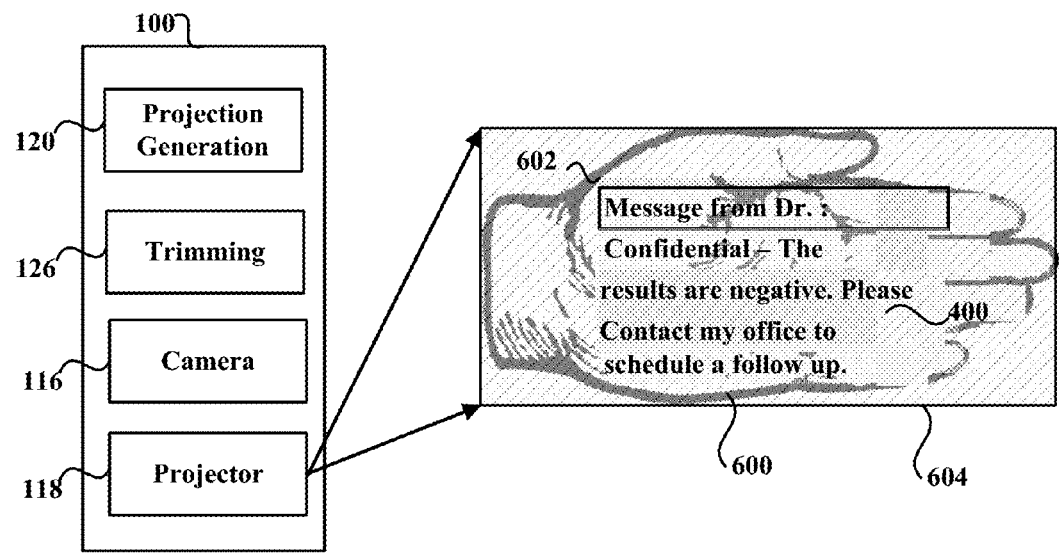

FIGS. 6A and 6B illustrate an example of trimming content to fit within the bounds of a hand 600. In some embodiments, processing component 106 of system 100 may generate one or more alerts, message, or other content. A user of system 100 may want to project content associated with the generated one or more alerts, messages, or other content, but may want to keep the content private. For example, if a user of system 100 receives a message via e-mail, instant message, or short messaging service (SMS) that includes personal information, the user may not want the personal information to be viewed by others. Consequently, the user may want to trim the content to be projected onto an object that allows the user to project the content at a suitable resolution without the projected content spilling onto surfaces beyond the object. Consequently, embodiments as shown herein may allow for a user to project content onto an object, such as their hand, while void areas are generated outside the object to keep the projected content private and not intrusive to others around the user.

As shown in FIG. 6A, camera 116 may capture one or more images of hand 600. The one or more captured images may then be used for projection generation 120, object recognition 122, tracking 124, and trimming 126. In some embodiments, images of hand 600 may be received by system 100 or may be stored in memory component 108. Trimming 126 may determine a shape of hand 600, an outline of hand 600, a distance to hand 600, and determine a void area and a content area for projection onto 600. As shown in FIG. 6B, projector 118 may project message 602 onto hand 600 such that message 602 is projected within the bounds of hand 600 and void area 604 is generated and, in some embodiments projected, outside the bounds of hand 600. As a result, the projected content, which as shown in FIG. 6B is a personal message 602, will only be projected onto hand 600 and any information in message 602 will not spill onto surface beyond hand 600 where others could view the information in personal message 602.

FIGS. 7A-7D illustrate an example of trimming content based on a detected gesture, consistent with some embodiments. As described previously, gesture detection 128 may include detecting gestures by processing a series of images or other information captured by camera 116 and/or sensors 114 to detect an abrupt change in a statistic of data captured by camera 116 and/or sensors 114 or detecting movement over time using ultrasonic waves. The detected gestures may then be correlated to an action or command using, for example, a gesture library included in gesture detection 128 or stored in memory component 108.

Figure 7A:
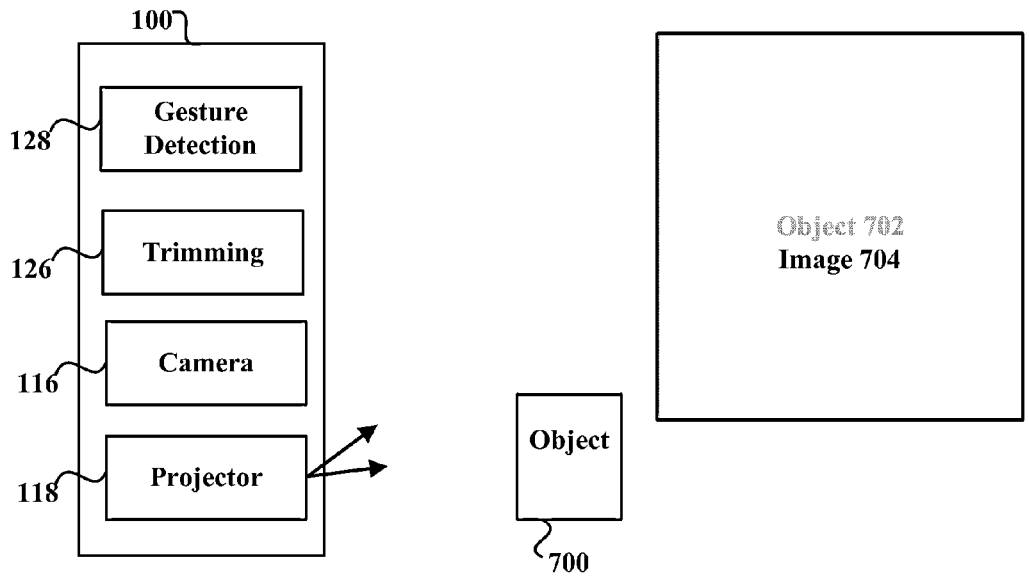
FIGS. 7A-7D illustrate an example of trimming content based on a detected gesture, consistent with some embodiments.

As shown in FIG. 7A, a user of system 100 may be in an area having a first object 700 and a second object 702. As depicted, first object 700 may be closer to system and smaller than second object 702, but embodiments consistent with this disclosure may not be so limiting. Projector 118 may be projecting an image 704 onto second object 702. In some embodiments, image 704 may be part of content generated by projection generation 120 determined by object recognition 122, and may be projected at a location on second object 702 determined by tracking 124. When a user of system 100 wants to project image 704 onto first object 700, the user may make a gesture that may be detected by camera 116 and/or sensors 114 and may be processed by gesture detection 128 to correlate the gesture to an action, such as projecting image 704 onto first object 700. The detected gesture may be a gesture such as a closed hand, indicating a closed or private mode. Gesture detection 128 may correlate this gesture into a command for projecting onto a different target or switching to a private mode, or other action indicative of switching projection targets.

Figure 7B:
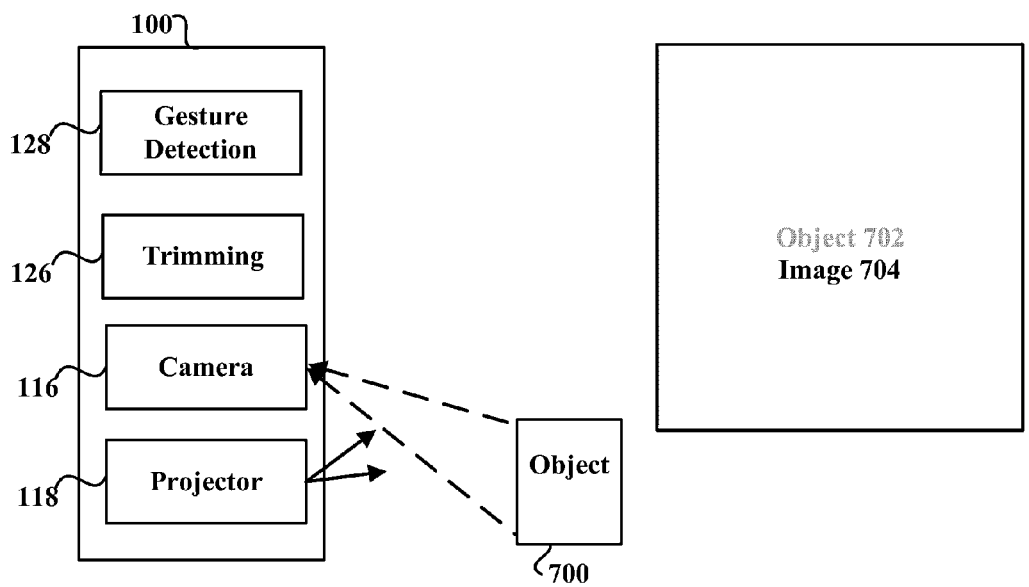
Figure 7C:
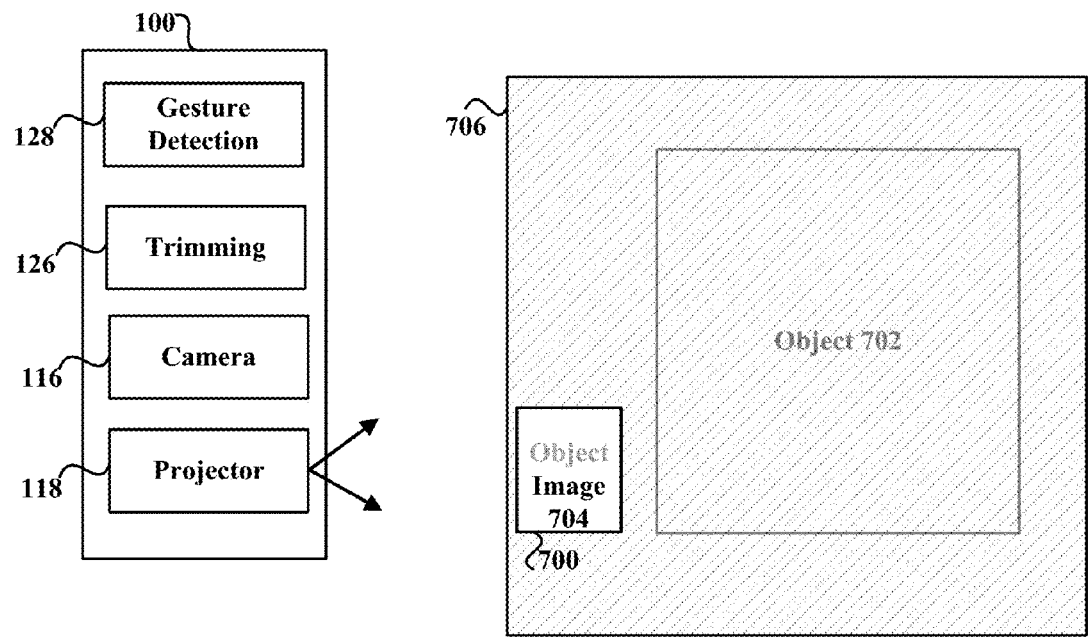

As shown in FIG. 7B, camera 116 may capture an image of first object 700 which may be used by trimming 126 to determine a scaling factor to scale image 704 and determine a content area and a void area. As shown in FIG. 7C, the scaling factor, determined content area and void area may be used by projection generation 120 to project image 704 at a resolution determined by the scaling factor within the determined content area a void area 706 is generated to mask areas outside of the content area. In some embodiments, first object 700 may be closer to the user of system 100 and, thus, may be more convenient for user for viewing image 704. First object 700 may also provide more privacy to the user of system 100, such that others around the user are not able to view image 704 when it is projected on object 700.

In some embodiments, first object 700 may also be determined as being a suitable for projecting image 704 onto based on object recognition 122. For example, in response to the gesture for switching projection targets, object recognition 122 may process one or more images captured by camera 116 to find a suitable object for a projection target based on factors such as distance to system 100, size, dimensions, etc. Trimming 126 may then determine the scaling factor, the content area and the void area 706 based on first object 700 recognized by object recognition 122.

Figure 7D:
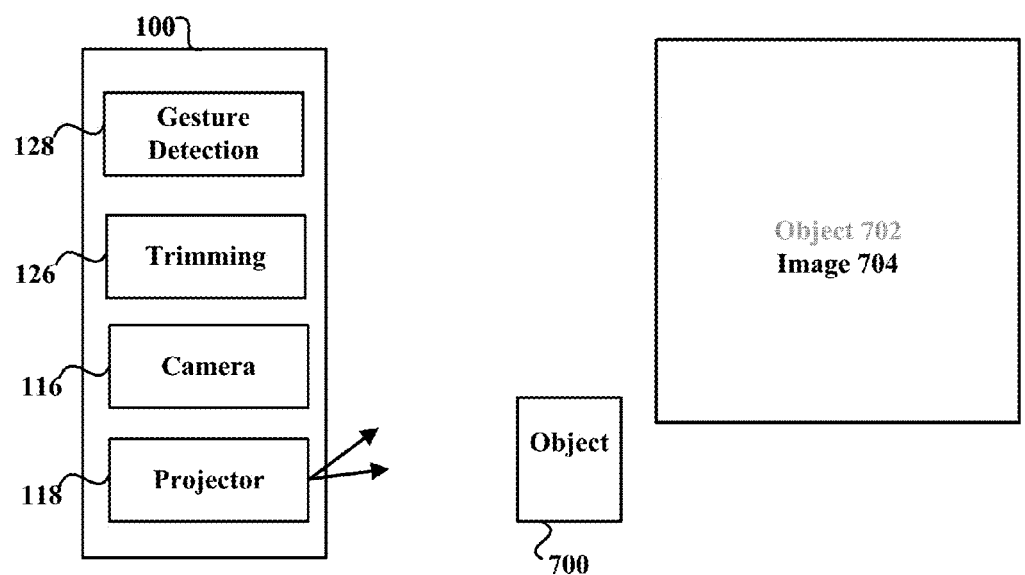

When the user of system 100 wants to switch projection targets from first object 700, user may make another gesture. For example, the user may make a gesture of opening their hand indicating public or open mode, or making a throwing motion towards second object 702 (or other desired target object). Camera 116 and/or sensors 114 may detect this gesture which may be correlated by gesture detection 128 to an action such as switching projection targets. As shown in FIG. 7D, projector 118 may then again project image 704 on second object 702. In some embodiments, image 704 may be projected onto second object 702 without trimming 126, i.e. without a void area or unmasked, such that image 704 is projected based on the specification of projector 118 and a distance between second object 702 and projector 118. In some embodiments, trimming 126 may determine a scaling factor, a content area and a void area 706 based on one or more images that include second object 702. In some embodiments, any scaling factors, content areas and void areas determined for previously projecting image 704 onto second object 702 may be saved and retrieved by projection generation 120 for projecting image 704 onto second object 702.

Figure 8A:
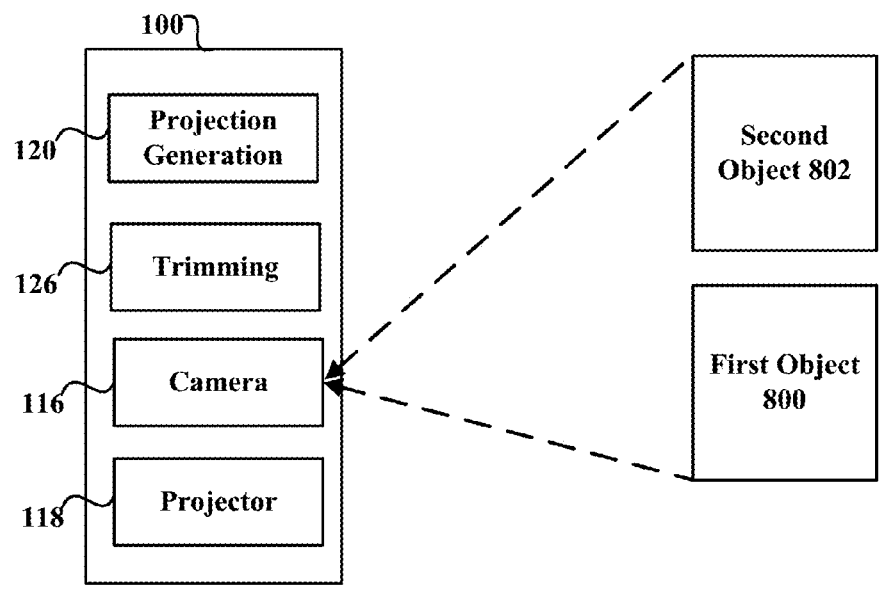
FIGS. 8A and 8B illustrate an example of trimming content to fit on multiple objects, consistent with some embodiments.
Figure 8B:
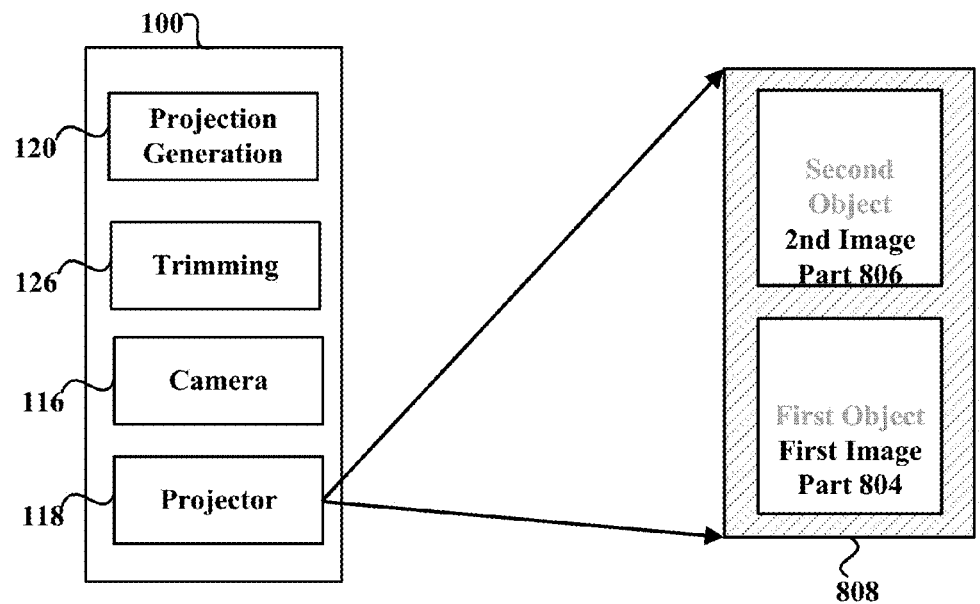

FIGS. 8A and 8B illustrate an example of trimming content to fit on multiple objects, consistent with some embodiments. In particular, the example shown in FIGS. 8A and 8B illustrate an example of trimming a single image to be displayed on first object 800 and second object 802. As shown in FIG. 8A, camera 116 may capture one or more images of first object 800 and second object 802. The one or more captured images may then be used for projection generation 120, object recognition 122, tracking 124, and trimming 126. In some embodiments, images of first object 800 and second object 802 may be provided to system 100 or may have been stored in memory component 108 of system 100. Object recognition 122 may determine content such as an image having a first image part 804 and a second image part 806 for respectively projecting onto first object 800 and second object 802. In some embodiments, a user of system 100 may designate an image for projection onto first object 800 and second object 802 and even designate which image part to display on each object. Moreover, object recognition 122 may recognize and determine first object 800 and second object 802 as content areas for first image part 804 and second image part 806, respectively. For example, if the image that is formed by first image part 804 and second image part 806 is too large for proper display on only one of first object 800 or second object 802, object recognition 122 may attempt to determine a second object of first object 800 or second object 802 and determine that the image is better displayed as a first image part 804 and a second image part 806 respectively projected on first object 800 and second object 802 and designate the face or side of first object 800 and second object 802 as content areas.

Trimming 126 may determine a shape of first object 800 and second object 802, a shape and/or an outline of first object 800 and second object 802, a distance to first object 800 and second object 802, and determine a void area 808 and a content area for projection of first image part 804 and second image part 806. As shown in FIG. 8B, projector 118 may project first image part 804 on first object 800 and second image part 806 on second object 802. Projector 118 may also project void area 808 around and first object 800 and second object 802 and between first object 800 and second object 802 such that the image formed by first image part 804 and second image part 806 is only projected on first object 800 and second object 802. In some embodiments, void area 808 may correspond to a virtual light mask that includes projected black or dark pixels or pixels which have been turned off by projector 118 so that no content or light is projected by projector 118 at those pixels.

Figure 9A:
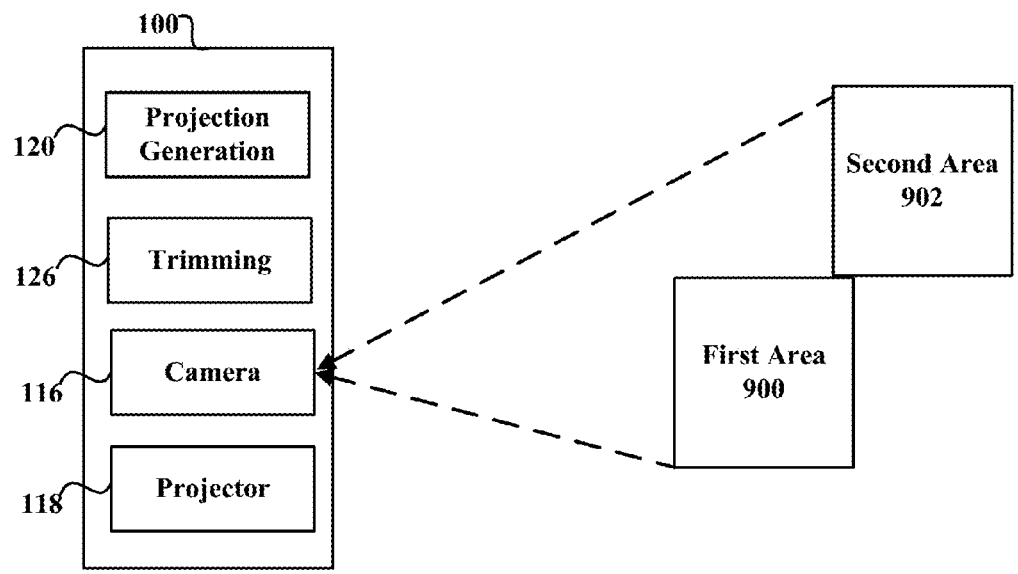
FIGS. 9A and 9B illustrate an example of trimming content to fit on multiple parts of an object, consistent with some embodiments.
Figure 9B:
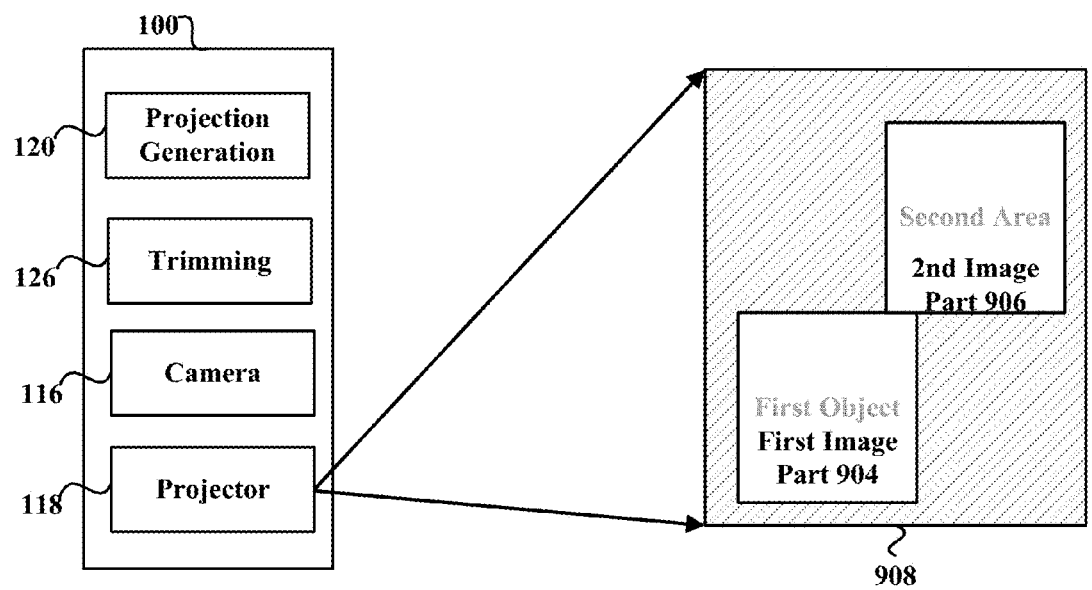

FIGS. 9A and 9B illustrate an example of trimming content to fit on multiple parts of an object, consistent with some embodiments. In particular, the example shown in FIGS. 9A and 9B illustrate an example of trimming a single image to be displayed on first area 900 and second area 902. As shown in FIG. 9A, camera 116 may capture one or more images of first area 900 and second area 902. The one or more captured images may then be used for projection generation 120, object recognition 122, tracking 124, and trimming 126. In some embodiments, images of first area 900 and second area 902 may be provided to system 100 or may have been stored in memory component 108 of system 100. Object recognition 122 may determine content such as an image having a first image part 904 and a second image part 906 for respectively projecting onto first area 900 and second area 902. In some embodiments, a user of system 100 may designate an image for projection onto first area 900 and second area 902 and even designate which image part to display on each area. Moreover, object recognition 122 may recognize and determine that the object having first area 900 and second area 902 is made up of multiple areas and determine first area 900 and second area 902 as content areas for first image part 904 and second image part 906, respectively.

Trimming 126 may determine a shape of first area 900 and second area 902, a shape and/or an outline of first area 900 and second area 902, a distance to first area 900 and second area 902, and determine a void area 908 and a content area for projection of first image part 904 and second image part 906. As shown in FIG. 9B, projector 118 may project first image part 904 on first area 900 and second image part 906 on second area 902. Projector 118 may also project void area 908 around and first area 900 and second area 902 such that the image formed by first image part 904 and second image part 906 is only projected on first area 900 and second area 902. In some embodiments, void area 908 may correspond to a virtual light mask that includes projected black or dark pixels or pixels which have been turned off by projector 118 so that no content or light is projected by projector 118 at those pixels.

Figure 10A:
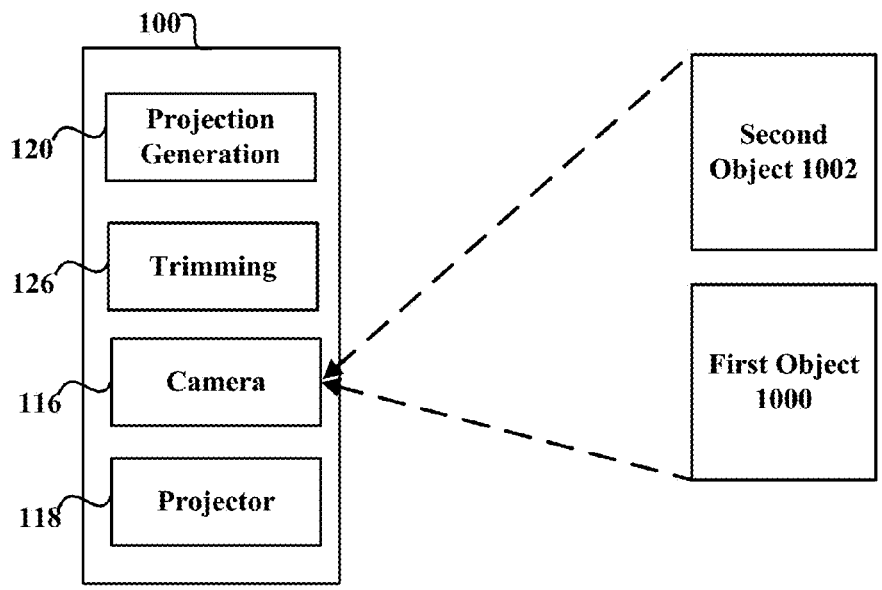
FIGS. 10A and 10B illustrate an example of trimming content having multiple images to fit on multiple objects, consistent with some embodiments.
Figure 10B:
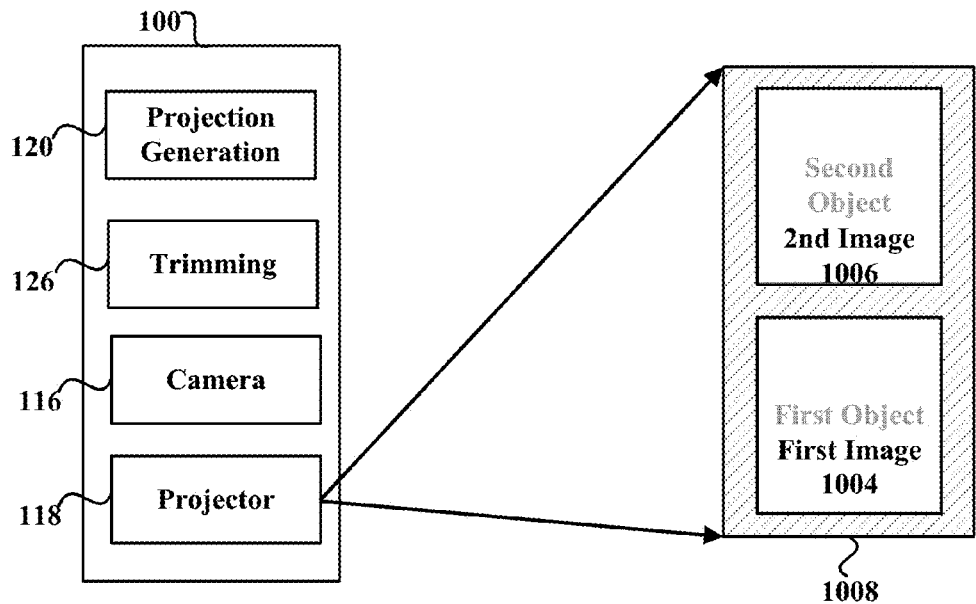

FIGS. 10A and 10B illustrate an example of trimming content having multiple images to fit on multiple objects, consistent with some embodiments. In particular, the example shown in FIGS. 10A and 10B illustrate an example of trimming a first image 1004 to be displayed on first object 1002 and a second image 1006 to be displayed on second object 1002. As shown in FIG. 10A, camera 116 may capture one or more images of first object 1000 and second object 1002. The one or more captured images may then be used for projection generation 120, object recognition 122, tracking 124, and trimming 126. In some embodiments, images of first object 1000 and second object 1002 may be provided to system 100 or may have been stored in memory component 108 of system 100. Object recognition 122 may determine content such as first image 1004 and a second image 1006 for respectively projecting onto first object 1000 and second object 1002. In some embodiments, a user of system 100 may designate first image 1004 and second image 1006 for projection onto first object 1000 or second object 1002. Moreover, object recognition 122 may recognize and determine first object 1000 and second object 1002 as content areas for first image part 1004 and second image part 1006, respectively.

Trimming 126 may determine a shape of first object 1000 and second object 1002, a shape and/or an outline of first object 1000 and second object 1002, a distance to first object 1000 and second object 1002, and determine a void area 1008 and a content area for projection of first image 1004 and second image 1006. As shown in FIG. 10B, projector 118 may project first image 1004 on first object 1000 and second image part 1006 on second object 1002. Projector 118 may also project void area 1008 around and first object 1000 and second object 1002 and between first object 1000 and second object 1002 such that first image 1004 and second image 1006 are only respectively projected on first object 1000 and second object 1002. In some embodiments, void area 1008 may correspond to a virtual light mask that includes projected black or dark pixels or pixels which have been turned off by projector 118 so that no content or light is projected by projector 118 at those pixels. Consequently, trimming 126 may allow projection generation 120 to generate a single projection that includes first image 1004, second image 1006, and void area 1008 for projection by projector 118 that appears as two discrete images on two objects to a user.

In some embodiments, the movement of first object 1000 and second object 1002 over time may be determined by receiving images from camera 116 or elsewhere of the area including first object 1000 and second object 1002 such that tracking 124 can maintain the projection of first image 1004 on first object 1000 and the projection of second image 1006 on second object 1002. Tracking 124 may also maintain the generation of void area 1008 such that first image 1004 and second image 1006 are only projected on first object 1000 and second object 1002.

Figure 11:
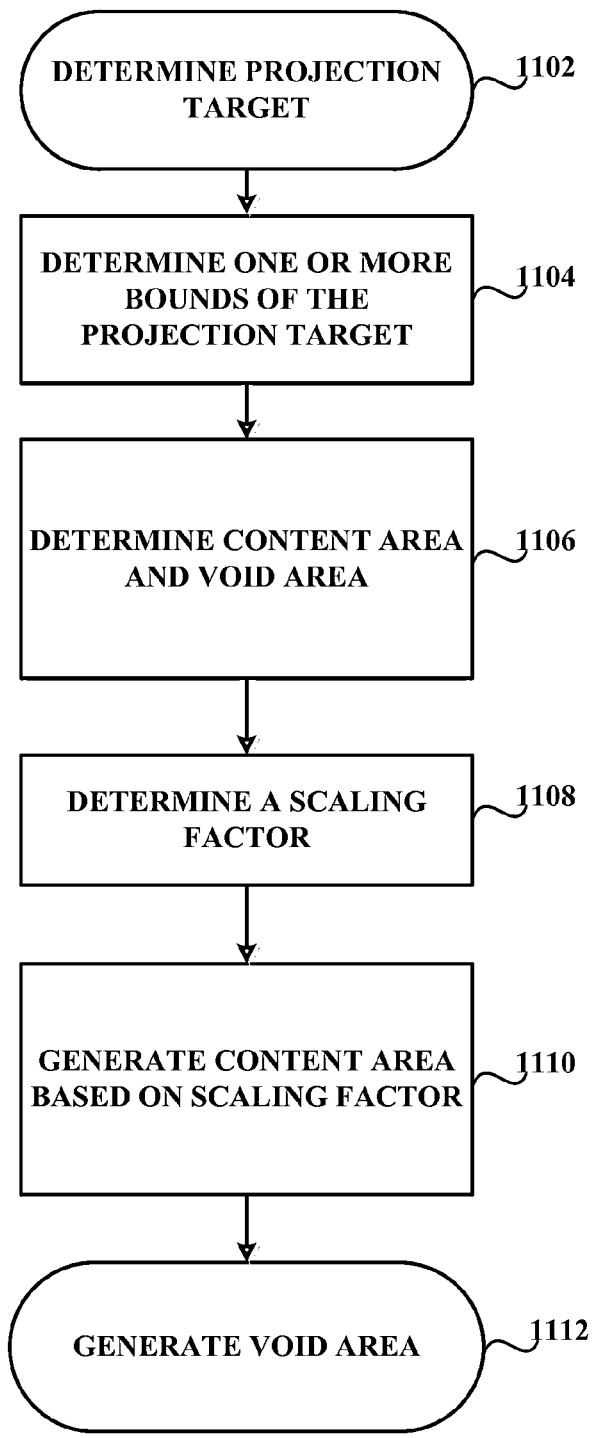
FIG. 11 is a flowchart illustrating a method for trimming content, consistent with some embodiments.

FIG. 11 is a flowchart illustrating a method for trimming content, consistent with some embodiments. For the purpose of illustration, FIG. 11 will be described with reference to any of FIGS. 1, 2A-2D, 3A-3B, 4A-4B, 5A-5B, and 6A-6B. The process 1100 shown in FIG. 11 may be embodied in computer-readable instructions for execution by one or more processors and, in some embodiments, may be implemented by an operating system of system 100 and may be implemented as a background service in the operating system. As shown in FIG. 11, process 1100 begins by determining a projection target (1102). In some embodiments, a projection target may be determined based on user input. For example, a user may designate a target displayed on display component 110 by selecting the target using input and navigation component 112. In some embodiments, a projection target may be determined using object recognition 122. For example, object recognition 122 may include determining a suitable projection target based on a shape or size of the target, or a type of surface of the target. Object recognition 122 may also include determining a projection target based on predetermined information associated with the target, as set by a content provider, retailer or manufacturer.

Once the projection target has been determined, one or more bounds of the projection target may be determined (1104). In some embodiments, the one or more bounds of the projection target may be determined by capturing one or more images of the projection target by camera 116, receiving images of the projection target, or retrieving images of the projection target from memory component 108. One or more characteristics of the projection target may then be determined based on the captured one or more images. For example, trimming 126 may determine a shape and outline of the projection target from the one or more images, as well as a distance to the projection target. In some embodiments, camera 116 may be or include a depth camera and may determine a depth map that may be used to determine a distance to the projection target. Moreover, a depth map may be used to determine a shape of the projection target by segmenting the projection target from the background in the depth map.

Based on the one or more bounds of the projection target, process 1100 may determine a content area and a void area (1106). In some embodiments, the content area may include areas within the projection target, and the void area may include the areas outside the projection target. For example, when determining one or more bounds of the projection target includes determining an outline of the projection target, determining the content area and the void area may include determining the area within the outline of the projection target as a content area and areas outside of the outline of the projection target as a void.

Process 1100 may then determine a scaling factor (1108). In some embodiments, determining a scaling factor may include determining a scaling factor based on a distance to the projection target such that the content projected on the projection target is projected at a predetermined resolution which may be a maximum resolution based on the bounds of the projection target. Projection generation 120 may then generate content for projection with the bounds of the determined content area based on the determined scaling factor (1110) and generate the void area (1112). In some embodiments, projector 118 may then project the generated content and the generated void area. In some embodiments, the projected void area may be projected dark pixels. In some embodiments, the void area may not be projected but instead projector 118 may turn off pixels within the void area. As a result, process 1100 may trim content for projection onto a projection target that does not spill onto surfaces or areas beyond the projection target. Process 1100 may be used to project content such as images onto objects such as shown in FIGS. 2A-2D, 3A-3B, 4A-4B, and 5A-5B. Moreover, process 1100 may be used to project messages onto a hand, such as shown in FIGS. 6A and 6B.

Figure 12:
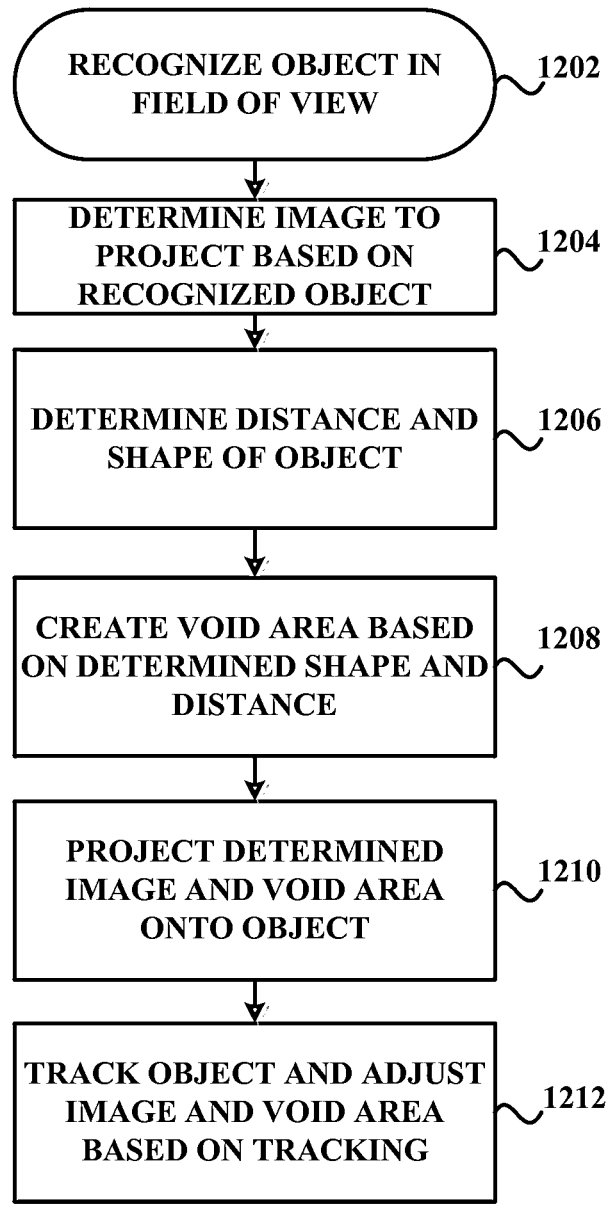
FIG. 12 is a flowchart illustrating a method for projecting a masked image on an object, consistent with some embodiments.

FIG. 12 is a flowchart illustrating a method for projecting a masked image on an object, consistent with some embodiments. For the purpose of illustration, FIG. 12 will be described with reference to FIGS. 3A-3B. Process 1200 shown in FIG. 12 may be embodied in computer-readable instructions for execution by one or more processors and, in some embodiments, may be implemented by an operating system of system 100 and may be implemented as a background service in the operating system. As shown in FIG. 12, process 1200 begins by recognizing an object in field of view (1202). For example, as shown in FIG. 3A, camera 116 may capture one or more images of object 300. In some embodiments, images of object may be received by system 100 or otherwise stored in memory component 108. Object recognition 122 may then include recognizing object 300 based on features of object 300 in the images. An image to project on the recognized object may then be determined (1204). In some embodiments, object recognition 122 may include determining content, such as an image, for projection on a recognized object based on information associated with the object. Referring again to FIG. 3A, object 300 may have certain features or characteristics that may benefit from the projection of image 302 thereon. For example, object 300 may be a product and image 302 may be an image associated with the product or information about the product. Object recognition 122 may include determining image 302 based on information stored locally within system, or information determined over a network. The information may be provided by user or may be provided by a third party such as a retailer, manufacturer, or content provider.

Process 1200 may then continue by determining a distance to an object and a shape of an object (1206). For example, trimming 126 may determine a shape and outline of object 300 from the one or more captured images, as well as a distance to object 300. In some embodiments, camera 116 may be or include a depth camera and may determine a depth map that may be used to determine a distance to object 300. Moreover, a depth map may be used to determine a shape of object 300 by segmenting the projection target from the background in the depth map.

Based on the determined shape and distance to object 300, trimming 126 may create a void area (1208). In some embodiments, the void area may include dark pixels that will be projected on areas outside the determined shape of object, such as void area 304. The void area may also correspond to pixels that turned off or otherwise not projected by projector 118. Process 1200 may then continue by projecting the determined image 302 and the void area 304 onto the object 300 (1210). Tracking 124 may then track object 300 and adjust void area 304 based on the tracking (1212). In some embodiments, tracking 124 includes detecting changes in a position or orientation of object 300 in six degrees-of-freedom based on information from sensors 114 and/or images received by system 100, stored in memory component 108, or captured by camera 116. Process 1200 may trim an image for projection onto an object such that the projected image is not projected onto surfaces or areas beyond the object. Although process 1200 has been described with respect to FIGS. 3A and 3B, process 1200 may further include designating a projection target within an object, such as shown in FIGS. 2A-2D, 3A-3B, 4A-4B, and 5A-5B. Moreover, the object may be a hand, and the image may be a message, such as shown in FIGS. 6A and 6B. In some embodiments, the object may be other objects such as a notebook, a computing device, a screen, a piece of paper, a box, a card, or other such objects. Moreover the image may also be other content including a picture, video, social networking post, calendar alert, user interface elements, and the like.

Figure 13:
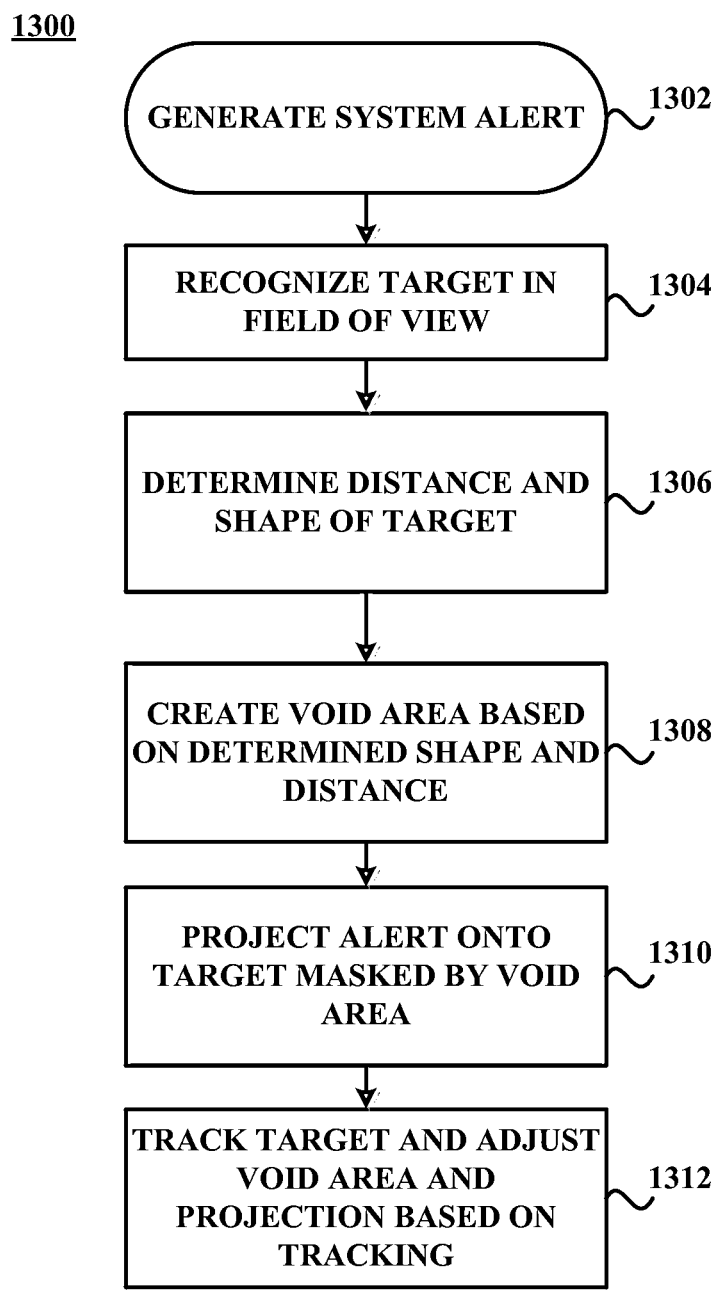
FIG. 13 is a flowchart illustrating a method for projecting a masked alert on a target, consistent with some embodiments.

FIG. 13 is a flowchart illustrating a method for projecting a masked alert on a target, consistent with some embodiments. For the purpose of illustration, FIG. 13 will be described with reference to FIGS. 6A-6B. The process 1300 shown in FIG. 13 may be embodied in computer-readable instructions for execution by one or more processors and, in some embodiments, may be implemented by an operating system of system 100 and may be implemented as a background service in the operating system. As shown in FIG. 13, process 1300 begins when system 100 generates a system alert (1302). In some embodiments a system alert may include an alarm, a notification, a calendar alert, a received message, such as an e-mail, instant message, or short messaging service message (SMS), and the like. For example, as shown in FIG. 6B, the system alert may include message 602. Process 1300 may then continue by recognizing target in field of view (1304). For example, as shown in FIG. 6A, camera 116 may capture one or more images of hand 600. Object recognition 122 may then include recognizing hand 600 based on features of hand 600 captured in the one or more captured images or in images received by system 100 or stored in memory component 108.

Process 13000 may then continue by determining a distance and shape of the target (1306). For example, trimming 126 may include determining a shape and outline of hand 600 from the one or more images, as well as a distance to hand 600. In some embodiments, camera 116 may be or include a depth camera and may determine a depth map that may be used to determine a distance to hand 600. Moreover, a depth map may be used to determine a shape of hand 600 by segmenting the projection target from the background in the depth map.

Based on the determined shape and distance to hand 600, trimming 126 may create a void area (1308). In some embodiments, the void area may dark pixels that will be projected on areas outside the determined shape of object, such as void area 604. In some embodiments, the void area may be pixels that are not projected by projector 118 or otherwise turned off when projecting. Process 1300 may then continue by projecting the alert onto the target masked by the void area (1310). As shown in FIG. 6B, for example, message 602 and void area 604 may be projected onto hand 600 such that message 602 is only projected on hand 600. Tracking 124 may then track the target, such as hand 600, and adjust void area 604 based on the tracking (1312). In some embodiments, tracking 124 includes detecting changes in a position or orientation of hand 600 in six degrees-of-freedom based on information from sensors 114 and/or images received by system 100, stored in memory component 108, or captured by camera 116. Process 1300 may trim an alert for projection onto a target such that the projected alert is not projected onto surfaces or areas beyond the target.

Figure 14:
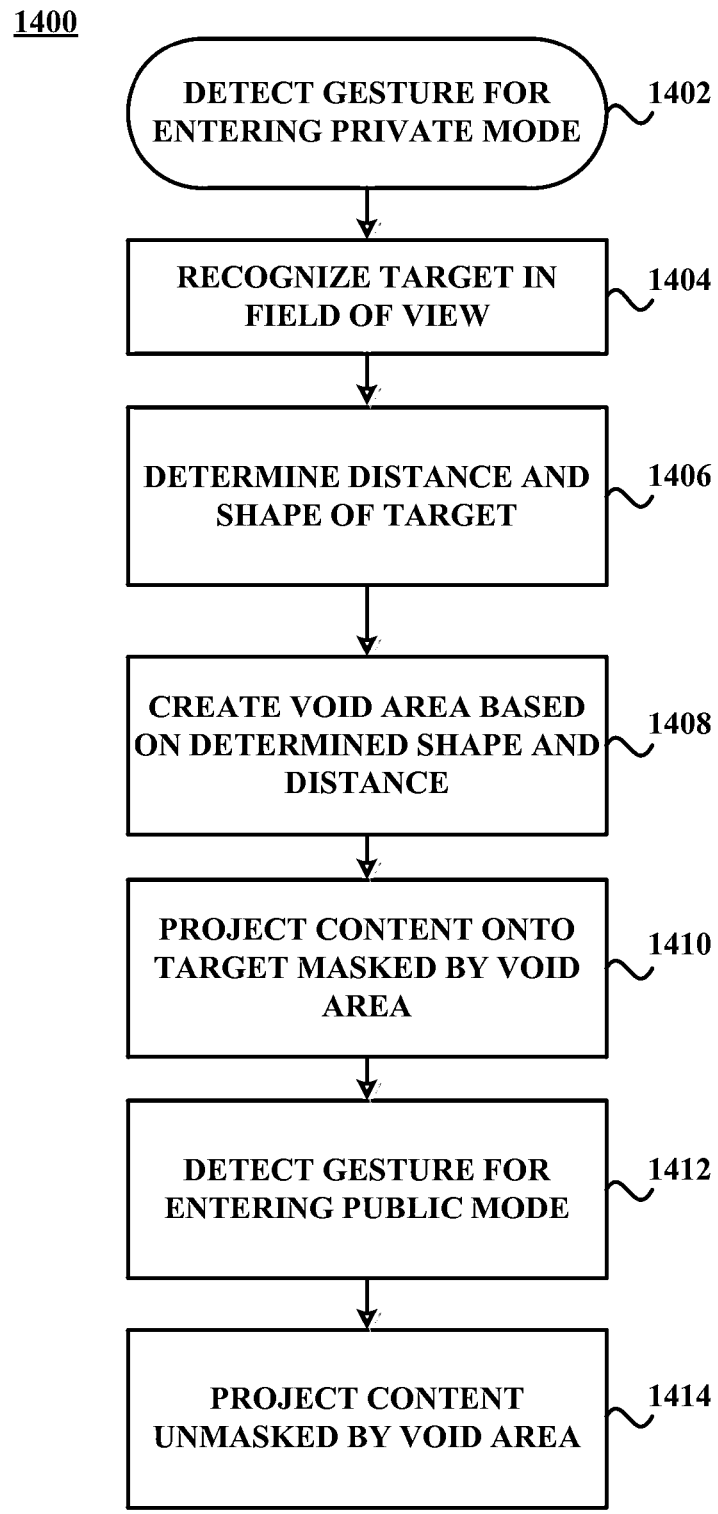
FIG. 14 is a flowchart illustrating a method for projecting a masked content on a target based on a detected gesture, consistent with some embodiments.

FIG. 14 is a flowchart illustrating a method for projecting a masked content on a target based on a detected gesture, consistent with some embodiments. For the purpose of illustration, FIG. 14 will be described with reference to FIGS. 7A-7D. The process 1400 shown in FIG. 14 may be embodied in computer-readable instructions for execution by one or more processors and, in some embodiments, may be implemented by an operating system of system 100 and may be implemented as a background service in the operating system. As shown in FIG. 14, process 1400 begins when gesture detection 128 detects a gesture for entering a private mode (1402). In some embodiments, a gesture for entering a private mode may be a closed hand, or other gesture that, when correlated with gestures in a gesture library, correspond to an action for entering a private mode. Process 1400 may then continue by recognizing target in field of view (1404). For example, as shown in FIG. 7B, camera 116 may capture one or more images of first object 700. In some embodiments, system 100 may receive images of first object 700 or may otherwise have one or more images of first object stored in memory component 108. Object recognition 122 may include recognizing first object 700 based on features of first object 700 from the images of first object 700.

Process 1400 may then continue by determining a distance and shape of the target (1406). For example, trimming 126 may include determining a shape and outline of first object 700 from the images, as well as a distance to first object 700. In some embodiments, camera 116 may be or include a depth camera and may determine a depth map that may be used to determine a distance to first object 700. Moreover, a depth map may be used to determine a shape of first object 700 by segmenting the projection target from the background in the depth map.

Based on the determined shape and distance to first object 700, trimming 126 may create a void area (1408). In some embodiments, the void area may include dark pixels that will be projected on areas outside the determined shape of first object 700, such as void area 706. In some embodiments, the void area may be pixels that are not projected by projector 118 or otherwise turned off when projecting. Process 1400 may then continue by projecting the content onto the target masked by the void area (1410). As shown in FIG. 7C, for example, image 704 and void area 706 may be projected such that image 704 is only projected on first object 700 and is masked by void area 706. Gesture detection may then detect a gesture for entering a public mode (1412). In some embodiments, the gesture for entering a public mode may be an open hand, a throwing motion, or other gesture that when detected is correlated to a gesture in a gesture library that corresponds to an action for entering a public mode. Projector 118 may then project the content unmasked by the void area (1414). For example, trimming 126 may determine no void area, determine a void area having no area or an area of zero, or may determine a the void area based on a larger target object, such as second object 702.

Software, in accordance with the present disclosure, such as program code and/or data, may be stored on one or more machine readable mediums, including non-transitory machine readable medium. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

Consequently, embodiments as described herein may provide systems and methods for fitting projections to a projection target by determining one or more bounds of the projection target and trimming the content for projection on the projection target based on the determined one or more bounds. Further, in order to maximize the resolution of the content for view on the projection target, embodiments described herein may determine areas of no content that are outside of the projection target, and project areas of no content, such as masked pixels, in these areas such that the content can be scaled to a predetermined resolution for projection onto the projection target without the projected content spilling onto surfaces and areas beyond the projection target. The examples provided above are exemplary only and are not intended to be limiting. One skilled in the art may readily devise other systems consistent with the disclosed embodiments which are intended to be within the scope of this disclosure. As such, the application is limited only by the following claims.

What is claimed is:

1. A method, comprising:
   determining a projection target by using object recognition to recognize an object in one more image frames, the object recognition based on information associated with the target;
   determining one or more bounds of the projection target;
   determining, by one or more processors, a content area where content is to be projected and a void area where no content is to be projected, the content area and the void area determined based on the one or more bounds, wherein the content area is further determined based on a designated content area associated with the object;
   determining, by the one or more processors, a scaling factor;
   generating content for projection within the content area based on the scaling factor; and
   generating the void area.

2. The method of claim 1, wherein determining one or more bounds of the projection target comprises:
   receiving one or more images of the projection target; and
   determining a shape of the projection target from the one or more images.

3. The method of claim 2, further comprising determining an outline of the projection target based on the determined shape of the projection target.

4. The method of claim 2, further comprising determining a depth map of an area including the projection target based on the one or more images.

5. The method of claim 4, wherein determining a scaling factor comprises determining a distance to the projection target based on the determined depth map.

6. The method of claim 4, wherein determining a shape of the projection target comprises segmenting the projection target out from a background in the determined depth map.

7. The method of claim 2, wherein generating the void area comprises creating a virtual mask based on the determined shape of the projection target.

8. The method of claim 1, further comprising projecting, by projector, the generated content on the projection target within the determined content area.

9. The method of claim 1, further comprising projecting, by a projector, the generated void area.

10. The method of claim 9, wherein projecting the generated void area comprises projecting dark pixels.

11. The method of claim 1, further comprising:
tracking the projection target; and
adjusting the determined content area and the determined void area based on the tracking.

12. The method of claim 1, further comprising:
detecting a gesture; and
determining, based on the detected gesture, the void area to have no area.

13. The method of claim 1, further comprising:
detecting a gesture;
determining a second projection target based on the detected gesture;
determining one or more bounds of the second projection target;
determining a second content area and a second void area based on the determined one or more bounds of the second projection target;
determining a second scaling factor based on a distance to the second projection target; and
projecting, by a projection device, content onto the second projection target within the determined content area.

14. An apparatus, comprising:
a projector configured to project a content area and a void area based on one or more projection parameters of a projection target, wherein the projection target is determined by using objection recognition to recognize an object in one more image frames, the object recognition based on information associated with the target, wherein the content area is further determined based on a designated content area associated with the object;
a camera configured to capture one or more images of a field of view including the projection target;
one or more processors coupled to the projector and the camera, the one or more processors configured to determine the one or more projection parameters; and
a memory coupled to the one or more processors.

15. The apparatus of claim 14, wherein the one or more processors are configured to determine the one or more projection parameters by processing the one or more images and determining a distance to the projection target, a shape of the projection target, and an outline of the projection target.

16. The apparatus of claim 14, wherein the void area comprises dark pixels projected outside of the determined outline of the content area.

17. The apparatus of claim 14, wherein the camera comprises at least one of a Digital Light Processing (DLP) projector, a laser beam-steering (LBS) projector, a liquid crystal on silicon (LCoS) projector.

18. The apparatus of claim 14, wherein the camera is further configured to capture gestures made by a user.

19. The apparatus of claim 18, wherein the gestures include gestures for switching between a private mode and a public mode.

20. A system, comprising:
means for determining a projection target, by using object recognition to recognize an object in one more image frames, the object recognition based on information associated with the target;
means for determining one or more bounds of the projection target;
means for determining a content area where content is to be projected and a void area where no content is to be projected based on the determined one or more bounds, wherein the content area is further determined based on a designated content area associated with the object;
means for determining a scaling factor;
means for generating content for projection within the content area based on the scaling factor; and
means for generating the void area.

21. The system of claim 20, wherein the means for determining one or more bounds of the projection target comprises:
means for receiving one or more images of the projection target; and
means for determining a shape of the projection target from the one or more images.

22. The system of claim 21, further comprising means for determining a depth map of an area including the projection target based on the one or more images.

23. The system of claim 20, further comprising a means for projecting the generated content on the projection target within the determined content area.

24. The system of claim 20, further comprising means for projecting the generated void area.

25. The system of claim 20, further comprising:
means for tracking the projection target; and
means for adjusting the determined content area and the determined void area based on the tracking.

26. The system of claim 20, further comprising:
means for detecting a gesture; and
means for determining, based on the detected gesture, the void area to have no area.

27. The system of claim 20, further comprising:
means for detecting a gesture;
means for determining a second projection target based on the detected gesture;
means for determining one or more bounds of the second projection target;
means for determining a second content area and a second void area based on the determined one or more bounds of the second projection target;
means for determining a second scaling factor based on a distance to the second projection target; and
means for projecting, by a projection device, content onto the second projection target within the determined content area.

28. A non-transitory computer-readable medium including instructions that when executed by one or more processors cause a system including the one or more processors to perform a method, comprising:
determining a projection target, by using object recognition to recognize an object in one more image frames, the object recognition based on information associated with the target, wherein the content area is further determined based on a designated content area associated with the object;
determining one or more bounds of the projection target;
determining, by one or more processors, a content area where content is to be projected and a void area where no content is to be projected based on the determined one or more bounds;
determining, by the one or more processors, a scaling factor; and
generating content for projection within the content area based on the scaling factor; and
generating the void area.

29. The method of claim 1, wherein the information associated with the target comprises at least one of information provided by a user, information provided by a content provider, information provided by a retailer, or information provided by a manufacturer.

30. The apparatus of claim 14, wherein the information associated with the target comprises at least one of information provided by a user, information provided by a content provider, information provided by a retailer, or information provided by a manufacturer.

31. The system of claim 20, wherein the information associated with the target comprises at least one of information provided by a user, information provided by a content provider, information provided by a retailer, or information provided by a manufacturer.

32. The non-transitory computer-readable medium of claim 28, wherein the information associated with the target comprises at least one of information provided by a user, information provided by a content provider, information provided by a retailer, or information provided by a manufacturer.

\* \* \* \* \*